US008926517B2

(12) United States Patent
Huang

(10) Patent No.: US 8,926,517 B2
(45) Date of Patent: Jan. 6, 2015

(54) FLEXIBLE MICRO-ELECTRO-MECHANICAL TRANSDUCER

(75) Inventor: Yongli Huang, San Jose, CA (US)

(73) Assignee: Kolo Technologies, Inc., San Jose, CA (US)

( * ) Notice: Subject to any disclaimer, the term of this patent is extended or adjusted under 35 U.S.C. 154(b) by 2114 days.

(21) Appl. No.: 11/425,128

(22) Filed: Jun. 19, 2006

(65) Prior Publication Data

US 2007/0013269 A1 Jan. 18, 2007

Related U.S. Application Data

(60) Provisional application No. 60/692,038, filed on Jun. 17, 2005, provisional application No. 60/705,606, filed on Aug. 3, 2005, provisional application No. 60/744,242, filed on Apr. 4, 2006.

(51) Int. Cl.
*A61B 8/14* (2006.01)
*B06B 1/06* (2006.01)
*H04R 19/00* (2006.01)
*B06B 1/02* (2006.01)
*B81B 3/00* (2006.01)
*G01N 29/24* (2006.01)
*H01L 41/09* (2006.01)

(52) U.S. Cl.
CPC ........... *B06B 1/0292* (2013.01); *H01L 41/0973* (2013.01); *B81B 3/0021* (2013.01); *G01N 29/2406* (2013.01)
USPC ............................ 600/459; 367/140; 367/181

(58) Field of Classification Search
USPC ............ 600/459, 437; 367/181, 140; 310/334
See application file for complete search history.

(56) References Cited

U.S. PATENT DOCUMENTS

| 5,186,177 | A | * | 2/1993 | O'Donnell et al. | ........... | 600/463 |
|---|---|---|---|---|---|---|
| 5,680,863 | A | * | 10/1997 | Hossack et al. | ............... | 600/459 |
| 6,613,005 | B1 | * | 9/2003 | Friedman et al. | ................. | 601/2 |
| 6,719,694 | B2 | * | 4/2004 | Weng et al. | .................... | 600/439 |
| 6,899,682 | B2 | * | 5/2005 | Eberle et al. | ................... | 600/459 |
| 7,030,536 | B2 | * | 4/2006 | Smith et al. | .................... | 310/309 |
| 7,305,883 | B2 | * | 12/2007 | Khuri-Yakub et al. | ......... | 73/579 |
| 7,514,851 | B2 | * | 4/2009 | Wilser et al. | .................. | 310/334 |
| 2004/0190377 | A1 | * | 9/2004 | Lewandowski et al. | ...... | 367/174 |
| 2005/0146247 | A1 | * | 7/2005 | Fisher et al. | .................. | 310/334 |

* cited by examiner

*Primary Examiner* — Katherine Fernandez
(74) *Attorney, Agent, or Firm* — Lee & Hayes, PLLC

(57) ABSTRACT

A curved or bendable micro-electro-mechanical transducer (such as the cMUT) is disclosed. The transducer has a plurality of transducer elements built on a substrate. The substrate has a slot below every two neighboring device elements. Each slot is at least at least partially filled with a flexible material to allow bending of the substrate. A bending actuator may be included to facilitate the bending of the substrate. An exemplary bending actuator uses a nonuniformly shrinkable material to bend the substrate. A curved or bendable cMUT of the present invention can be configured to be an intravascular ultrasound (IVUS) device.

39 Claims, 15 Drawing Sheets

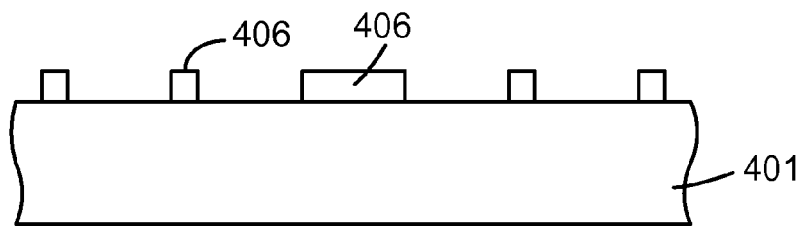
FIG. 4.1
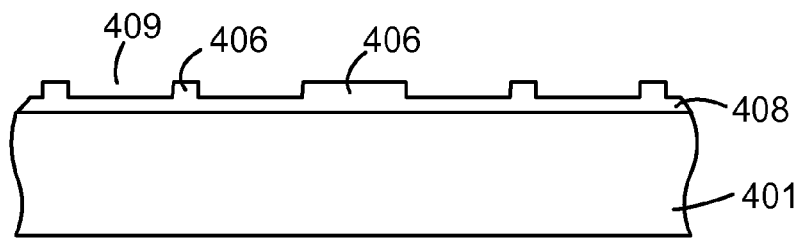
FIG. 4.2
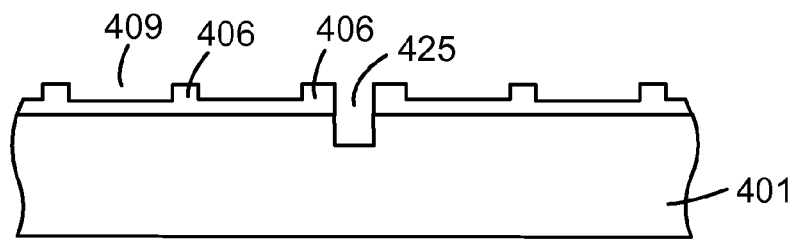
FIG. 4.3
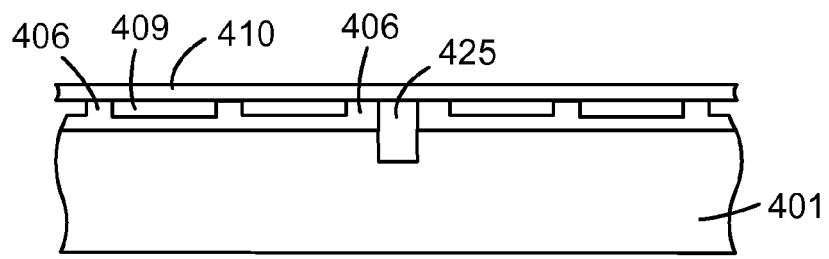
FIG. 4.4

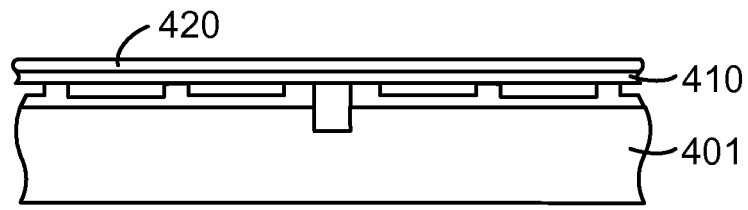
FIG. 4.5
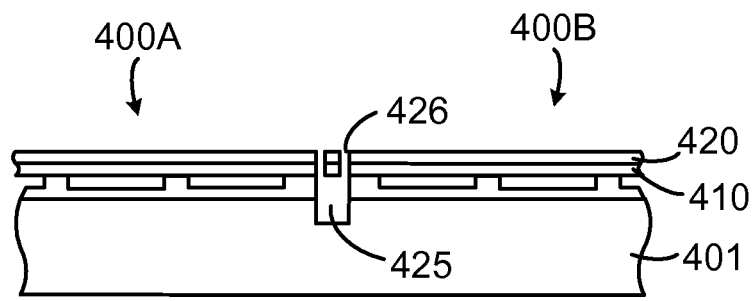
FIG. 4.6
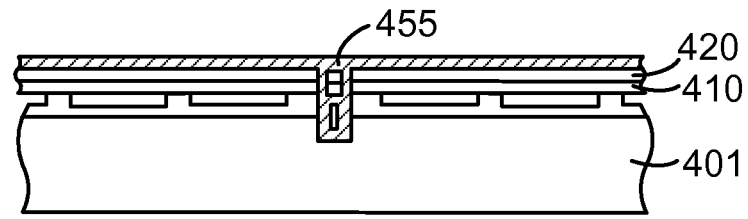
FIG. 4.7
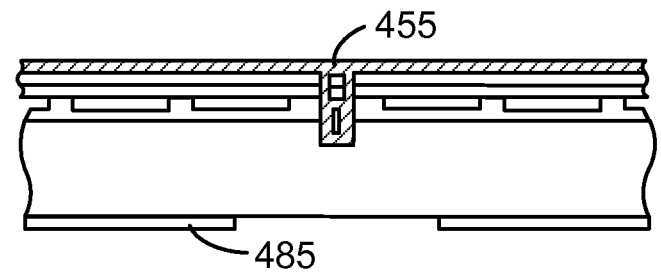
FIG. 4.8

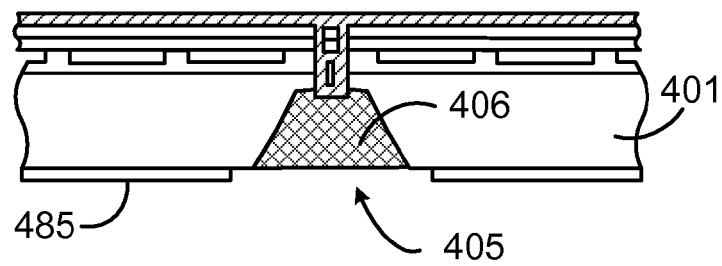
FIG. 4.9
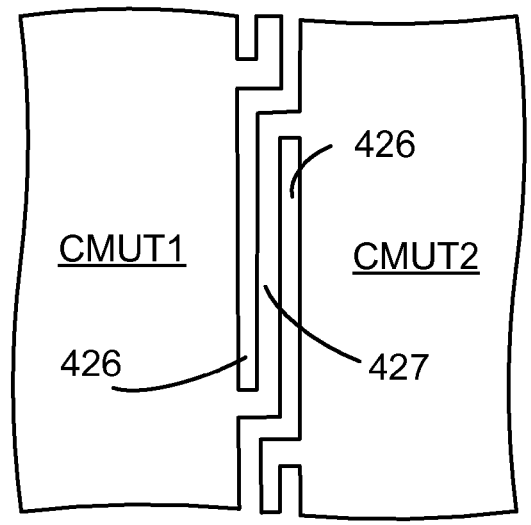
FIG. 4.6a
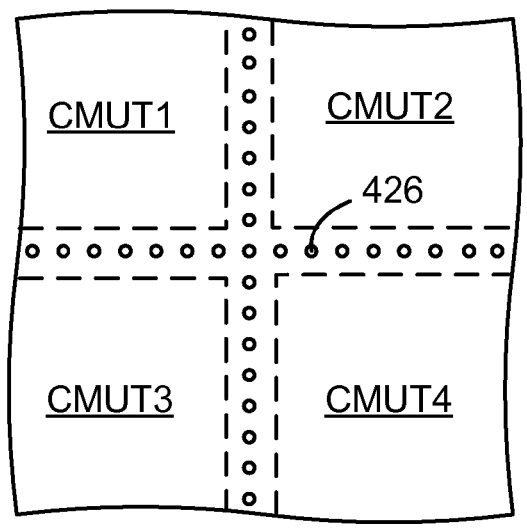
FIG. 4.6b

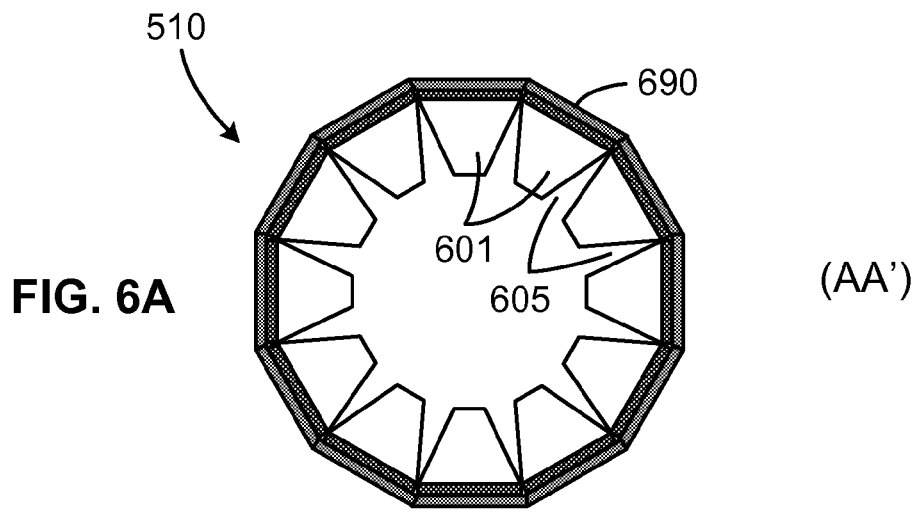
FIG. 6A (AA')
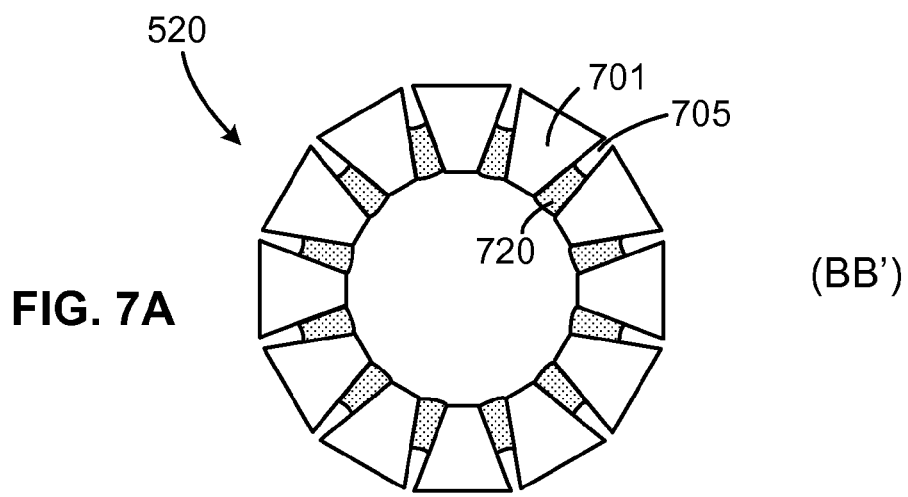
FIG. 7A (BB')
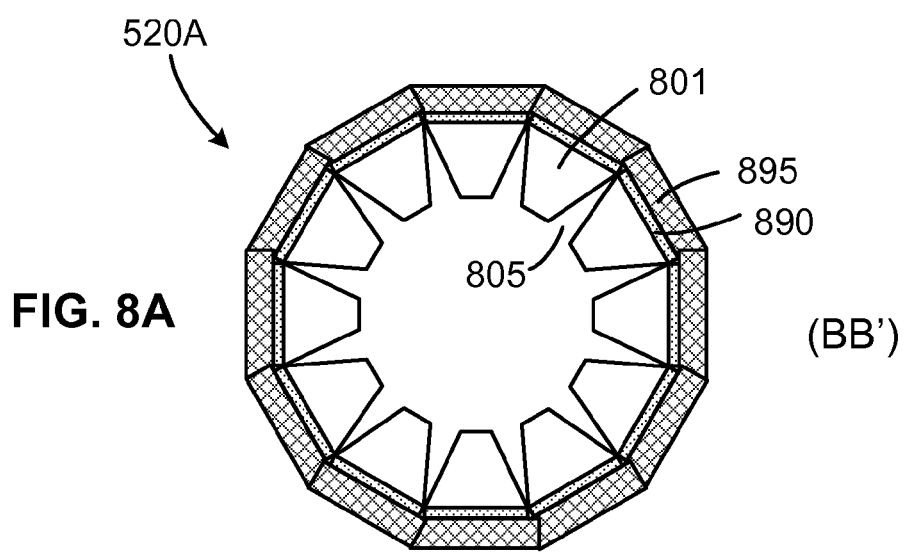
FIG. 8A (BB')

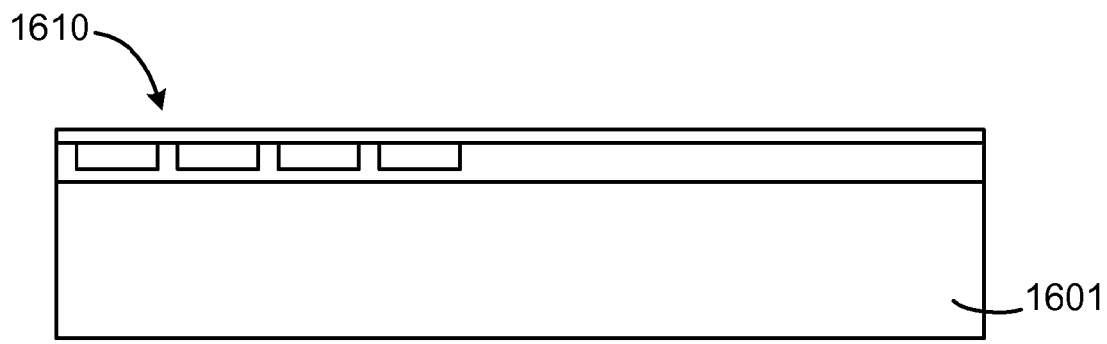
FIG. 16.1
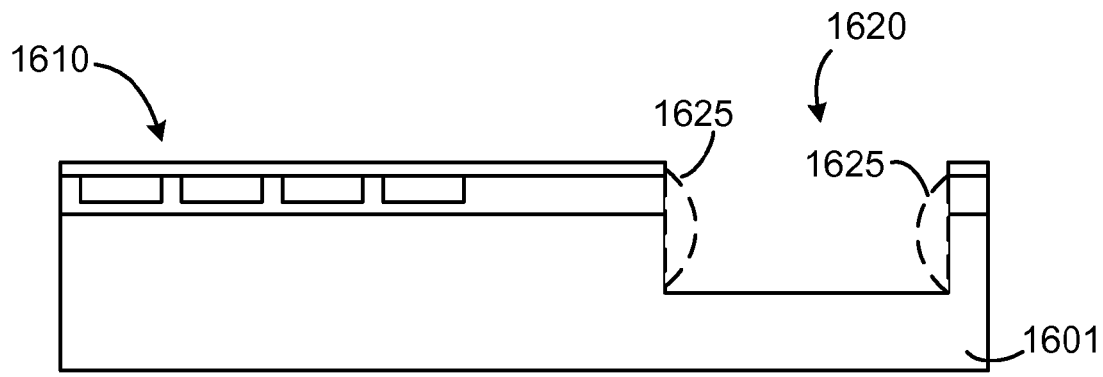
FIG. 16.2
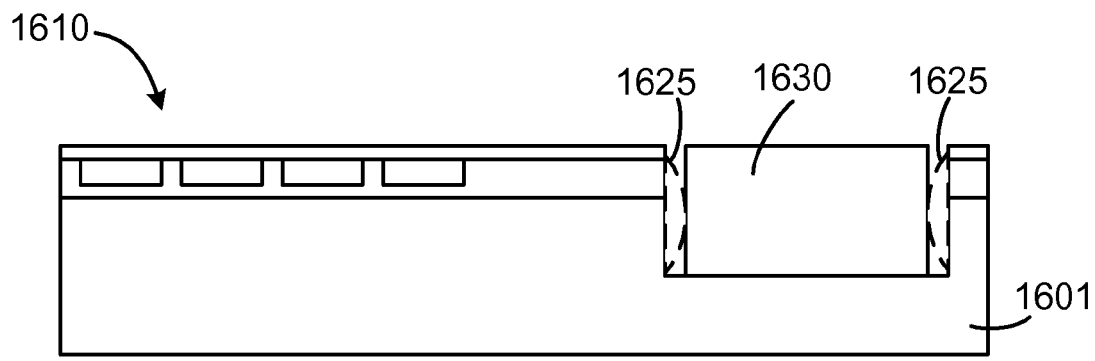
FIG. 16.3

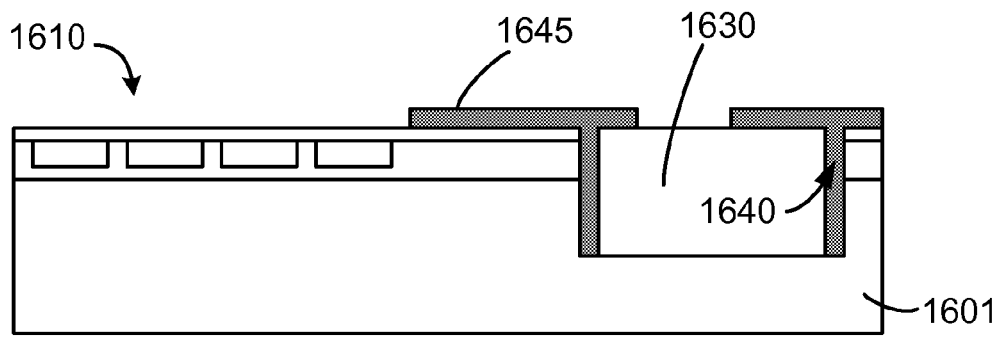
FIG. 16.4
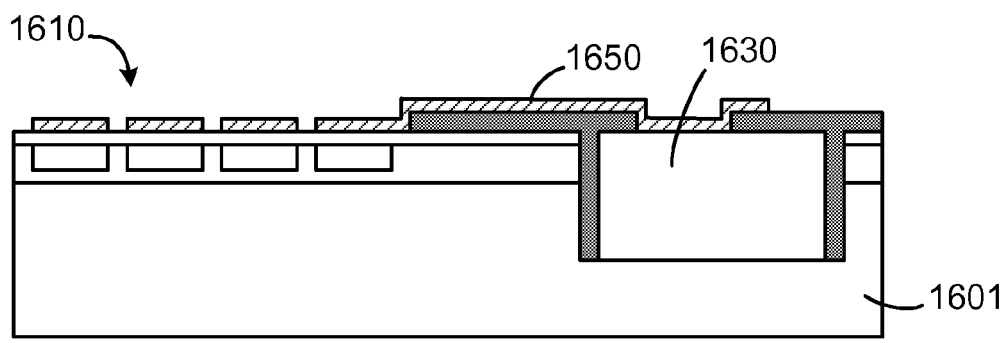
FIG. 16.5
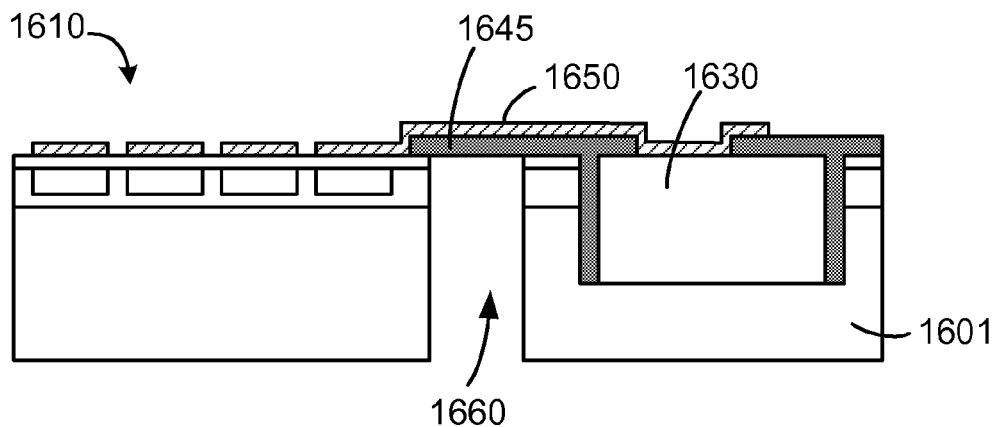
FIG. 16.6

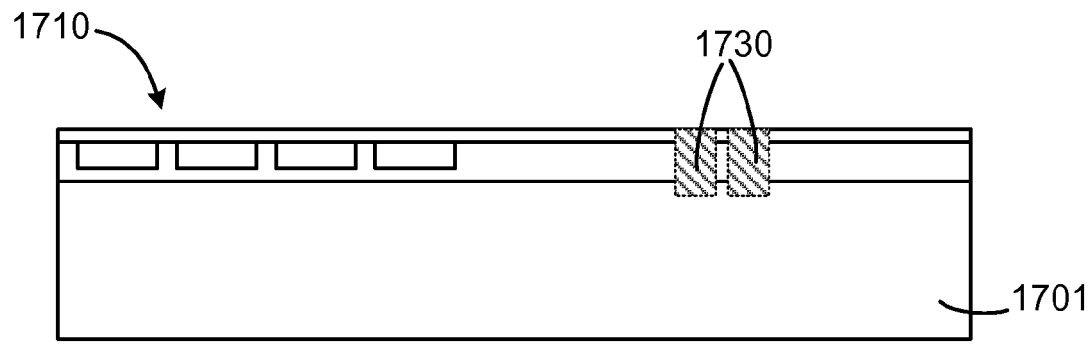
FIG. 17.1
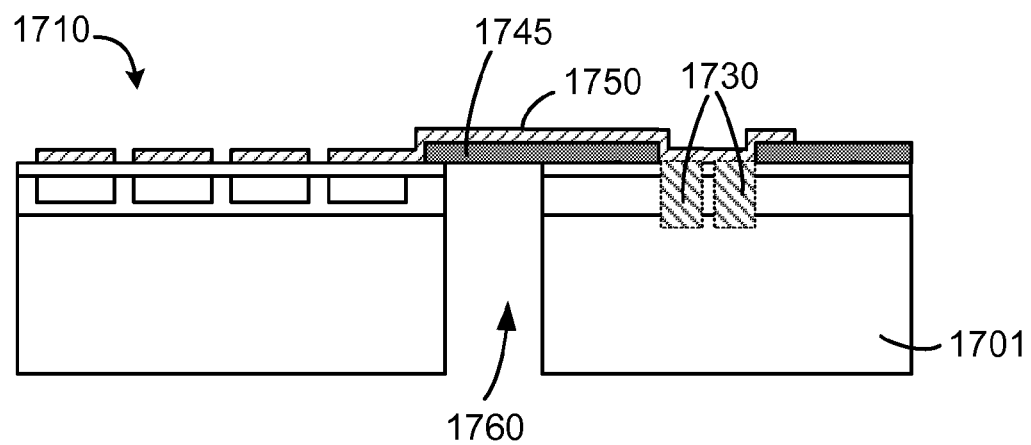
FIG. 17.2

FLEXIBLE MICRO-ELECTRO-MECHANICAL TRANSDUCER

CROSS-REFERENCE TO RELATED APPLICATIONS

This application claims priority from U.S. Provisional Application Ser. No. 60/692,038, filed Jun. 17, 2005; Ser. No. 60/705,606, filed Aug. 3, 2005; and Ser. No. 60/744,242, filed Apr. 4, 2006, which applications are incorporated herein by reference in their entirety.

This application further incorporates herein by reference in entirety the following:

International Application (PCT) No. PCT/IB2006/051566, entitled THROUGH WAFER INTERCONNECTION, filed on May 18, 2006;

International Application (PCT) No. PCT/IB2006/051567, entitled METHODS FOR FABRICATING MICRO-ELECTRO-MECHANICAL DEVICES, filed on May 18, 2006;

International Application (PCT) No. PCT/IB2006/051568, entitled MICRO-ELECTRO-MECHANICAL TRANSDUCERS, filed on May 18, 2006;

International Application (PCT) No. PCT/IB2006/051569, entitled MICRO-ELECTRO-MECHANICAL TRANSDUCERS, filed on May 18, 2006; and International Application (PCT) No. PCT/IB2006/051948, entitled MICRO-ELECTRO-MECHANICAL TRANSDUCER HAVING AN INSULATION EXTENSION, filed on Jun. 16, 2006.

BACKGROUND

1. Field of the Invention

The present invention relates to micro-electro-mechanical devices that have a movable mechanical part for energy transformation, particularly to micromachined ultrasonic transducers (MUT) such as capacitance micromachined ultrasonic transducers (cMUT).

2. Description of the Prior Art

Micro-electro-mechanical transducers usually share a common feature which includes a movable mechanical part used for energy transformation. One example of such micro-electro-mechanical transducers is micromachined ultrasonic transducers (MUT). An ultrasound transducer performs a chain of energy transformation to realize its function of a transducer. In its receiving mode, the acoustic energy of ultrasound waves propagating in a medium where the transducer is placed is transformed to mechanical energy of a movable part (conventionally a vibrating membrane) in the transducer. The motion of the movable part is then transformed to a detectable electromagnetic (usually electrical) signal. In its transmitter mode, the reverse chain of energy transformation takes place.

Various types of ultrasonic transducers have been developed for transmitting and receiving ultrasound waves. Ultrasonic transducers can operate in a variety of media including liquids, solids and gas. These transducers are commonly used for medical imaging for diagnostics and therapy, biochemical imaging, non-destructive evaluation of materials, sonar, communication, proximity sensors, gas flow measurements, in-situ process monitoring, acoustic microscopy, underwater sensing and imaging, and many others. In addition to discrete ultrasound transducers, ultrasound transducer arrays containing multiple transducers have been also developed. For example, two-dimensional arrays of ultrasound transducers are developed for imaging applications.

Compared to the widely used piezoelectric (PZT) ultrasound transducer, the MUT has advantages in device fabrication method, bandwidth and operation temperature. For example, making arrays of conventional PZT transducers involves dicing and connecting individual piezoelectric elements. This process is fraught with difficulties and high expenses, not to mention the large input impedance mismatch problem presented by such elements to transmit/receiving electronics. In comparison, the micromachining techniques used in fabricating MUTs are much more capable in making such arrays. In terms of performance, the MUT demonstrates a dynamic performance comparable to that of PZT transducers. For these reasons, the MUT is becoming an attractive alternative to the piezoelectric (PZT) ultrasound transducers.

Among the several types of MUTs, the capacitive micromachined ultrasonic transducer (cMUT), which uses electrostatic transducers, is widely used. A basic cMUT cell has a parallel plate capacitor consisting of a rigid bottom electrode and a top electrode residing on or within a flexible membrane that is used to transmit or receive an acoustic wave in the adjacent medium. A DC bias voltage is applied between the electrodes to deflect the membrane to an optimal position for cMUT operation, usually with the goal of maximizing sensitivity and bandwidth. During transmission, an AC signal is applied to the transducer. The alternating electrostatic force between the top electrode and the bottom electrode actuates the membrane in order to deliver acoustic energy into the medium surrounding the cMUT. During reception, the impinging acoustic wave vibrates the membrane, thus altering the capacitance between the two electrodes. An electronic circuit detects this capacitance change.

For certain applications, a flexible or curved cMUT array may be needed. For example, a cMUT array may need to be attached to a non-flat surface and therefore need to be flexible or bendable to conform to the non-flat surface. A flexible or curved cMUT array may also be advantageous for applications in very small confined areas. One important example is intravascular ultrasound (IVUS) devices. IVUS is used in an invasive medical procedure performed along with cardiac catheterization. An IVUS device is a miniature sound probe (transducer) on the tip of a coronary catheter threaded through the coronary arteries and, using high-frequency sound waves, produces detailed images of the interior walls of the arteries. IVUS is increasingly used by doctors to view the artery from the inside out, making it possible to evaluate the amount of disease present, how it is distributed, and in some cases, its composition.

The present curved cMUTs are difficult and expensive to fabricate due to lack of controllability and insufficient maneuverability. Furthermore, once fabricated the curved cMUTs have a fixed curvature that cannot be changed or controlled. Due to the importance of these MUT devices, it is desirable to improve the technology in terms of performance, functionality, and manufacturability in general, and to make possible a cMUT array that has a precise and controlled curvature in particular.

SUMMARY OF THE INVENTION

This patent application discloses a curved or bendable micro-electro-mechanical transducer (such as the cMUT). This patent application also discloses methods for fabricating the curved or bendable micro-electro-mechanical transducer. The inventive techniques may be used in both conventional membrane-based cMUTs and cMUTs having embedded springs transporting a top plate.

The transducer of the present invention has a plurality of transducer elements built on a substrate. The substrate has a slot below every two neighboring device elements. Each slot is at least partially filled with a flexible material to provide support to the structure of the transducer and to allow bending of the substrate. Each transducer element has a surface portion above the substrate. The surface portion includes a movable transducing member, and is spaced from the substrate to define a transducing gap between the movable transducing member and the substrate. A bent or bendable cMUT of the present invention can be configured to be an intravascular ultrasound (IVUS) device.

The plurality of the transducer elements may be arranged side-by-side in succession to form an elongated strap that is closable or closed at the two ends to form an enclosed shape such as a substantially cylindrical shape.

In one embodiment, a bending actuator is included to facilitate the bending of the substrate. The bending actuator may automatically bend the substrate upon experiencing a change of environment (such as temperature), receiving a signal, or undergoing a treatment (such as the thermal treatment). An exemplary bending actuator uses a material having a nonuniformly changeable size to bend the substrate. The material may be filled in the slots in the substrate underneath the transducer elements, or filled in slots in another portion of the substrate aside the transducer element. When the slots have nonuniform cross-sectional sizes, the material filled therein undergoes a nonuniform change of size and bends the substrate. Alternatively, the bending actuator may comprise a bimorph that is able to deflect and thus bend the substrate under a given condition.

Furthermore, trench openings between the surface portions of neighboring transducer elements may be formed to facilitate angling of the transducer elements during bending of the substrate. The trench openings also accurately define the separation between the elements (and thus the size of the transducer elements) to make the fabrication process easier. The trench openings may be filled with a desired filler material.

Flexible hinges may be formed across the trench openings between the surface portions of neighboring transducer elements. The flexible hinge may use a conductive material to electrically connect the neighboring transducer elements.

One important application of the micro-electro-mechanical transducer of present invention is a capacitive micromachined ultrasound transducer (cMUT) wherein the transducing member comprises a top electrode, and wherein the transducer further comprises a bottom electrode spaced from the top electrode. The cMUT may be based on conventional flexible membrane cMUT design in which the surface portion of each transducer element comprises a flexible membrane which has a perimeter secured on a support between the flexible membrane and the substrate. The cMUT may also be based on embedded spring cMUT (ESMUT or ESCMUT) in which the surface portion of each device member comprises: (1) a top plate; (2) a middle spring layer; and (3) a connector between the middle spring layer and the top plate. In an ESMUT, the top plate is placed over the connector, which separates the top plate from the middle spring layer, and the middle spring layer is placed over the substrate. The substrate and the middle spring layer define a cavity therebetween, the cavity is bordered by a standing feature having a sidewall, and the middle spring layer extends from the sidewall to cover the cavity. The top electrode may be part of the top plate, while the bottom electrode part of the middle spring layer and/or the substrate.

According to another aspect of the present invention, a method for making a flexible or bent micro-electro-mechanical transducer is disclosed. The method has two main steps: (1) fabricating a plurality of transducer elements on a substrate, each transducer element having a surface portion including a movable transducing member, the surface portion being spaced from the substrate to define a transducing gap between the movable transducing member and the substrate; (2) cutting a slot through a bottom surface of the substrate; and (3) filling the slot using a flexible material. The soft filler material provides support to the structure of the transducer during the fabrication process and maintains the integrity of the device after fabrication. The slot is preferably cut at a position between two neighboring transducer elements to allow bending of the substrate and angling of the surface portions of the neighboring transducer elements. The slot preferably has a shape with nonuniform cross-sectional sizes which generally increase from the top of the substrate to the bottom facing away the transducer elements.

In one embodiment, the method further comprises adding a bending actuation material into the slot on the substrate. One example of a bending actuation material is a material having a changeable size (such as a shrinkable are expandable material) which causes the substrate to be bent by a nonuniform change of size.

In another embodiment, the method further comprises introducing a bending actuator along the substrate. The bending actuator is adapted for automatically bending or changing the degree of bending of the substrate when the bending actuator is triggered upon experiencing a change of environment, receiving a signal, or undergoing a treatment. One example of the change of environment is a change of temperature. The substrate with the plurality of transducer elements is then bent by triggering the bending actuator.

The method may further comprise forming a trench opening between the surface portions of neighboring transducer elements to facilitate angling of the transducer elements during bending of the substrate.

The foregoing and other features and advantages will become more apparent from the following detailed description of several embodiments, which proceeds with reference to the accompanying figures.

BRIEF DESCRIPTION OF THE FIGURES

FIGS. 4.1-4.9 show an exemplary process for fabricating a flexible cMUT in accordance with the present invention.

FIGS. 16.1-16.6 show an exemplary process for fabricating a cMUT array integrated with IC components fabricated on a separate IC die.

FIGS. 17.1-17.2 show a direct fabrication process for fabricating a cMUT array integrated with IC components fabricated on the same substrate.

DETAILED DESCRIPTION OF THE INVENTION

Figure 1A:
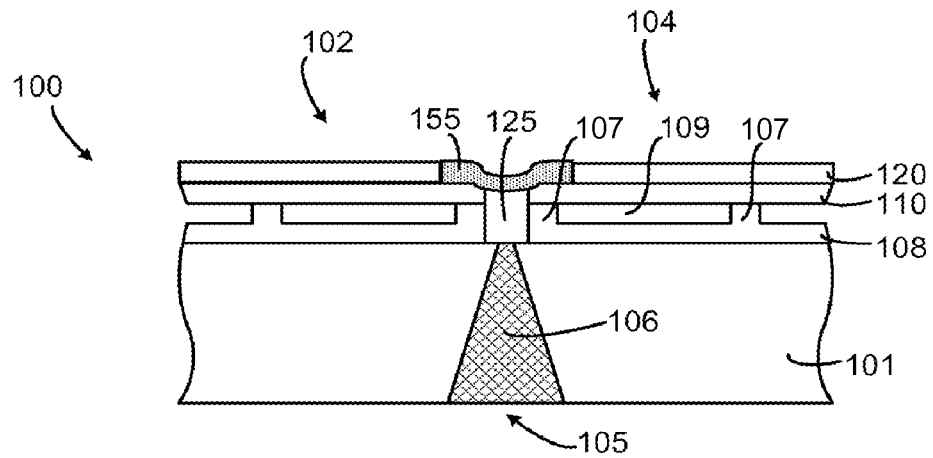
FIGS. 1A and 1B show an exemplary embodiment of the present invention improving a conventional membrane-based cMUT.

The micro-electro-mechanical transducer such as a capacitance micromachined ultrasonic transducer (cMUT) of the present invention will be described in detail along with the figures, in which like parts are denoted with like reference numerals or letters. The micro-electro-mechanical transducer may be fabricated using any suitable methods, particularly using the methods disclosed herein and in the several patent applications identified herein.

The invention has been described below with reference to specific embodiments. In most cases, a cMUT structure is used to illustrate the invention. It is appreciated, however, that the present invention is not limited to cMUTs. It will be apparent to those skilled in the art that various modifications may be made and other embodiments can be used without departing from the broader scope of the inventions. Therefore, these and other variations upon the specific embodiments are intended to be covered by the present inventions. Those skilled in the art will recognize that various features disclosed in connection with the embodiments may be used either individually or jointly.

In this document, a conductive material is defined as one having a resistivity less than $1 \times 10^4$ $\Omega$-cm. Silicon and polysilicon materials are therefore considered conductive materials in this context. A good conductive material preferably has a resistivity less than 1 $\Omega$-cm. The terms "insulation material", "insulating material" and "dielectric material" are used interchangeably unless noted otherwise, and are defined as one having a resistivity greater than $1 \times 10^4 \Omega$-cm. A good insulation/insulating material preferably has a resistivity greater than $1 \times 10^8$ $\Omega$-cm. An insulator generally comprises an insulating material, but in special cases may include air or vacuum.

It is noted that the terms "transducer" and "transducing member" are used in a broad sense in the present description to not only include devices that perform both actuation and sensing functions but also include devices that perform either an actuation function or an sensing function. The term "flexible" is used in its broadest sense. A flexible material or component is changeable or variable in at least one aspect of its physical size, shape, or orientation, including bendable, soft, pliable, distortable, stretchable, compressible, shrinkable, and expandable.

A micro-electro-mechanical transducer generally has a substrate and a surface portion above the substrate. The surface portion usually has a movable transducing member. The surface portion may have different structures in different designs of the transducer. In some designs, the surface portion may be a multilayered structure.

Figure 1B:
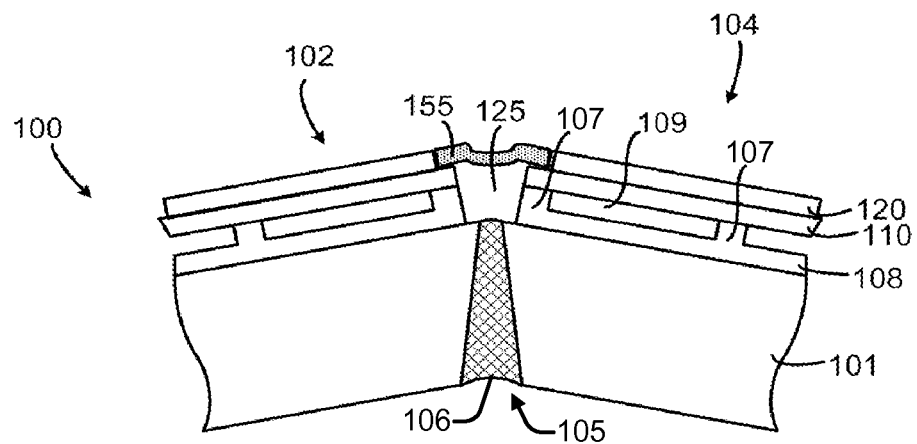

FIGS. 1A and 1B show an exemplary embodiment of the present invention improving a conventional membrane-based cMUT. The cMUT structure 100 is a portion of a complete cMUT structure having a plurality of transducer elements built on a substrate 101. Shown in cMUT structure 100 are a first cMUT element 102 and a neighboring second cMUT element 104, each having a laminated surface portion including a membrane layer 110 and a top electrode 120. The boundary of the cMUT element 102 and the neighboring cMUT element 104 is defined by a separation trench 125 formed through the surface portion (the membrane layer 110 and the top electrode 120), and further through an insulating support 107 which stands on an insulation layer 108 deposited on the substrate 101. It is appreciated that the separation trench 125 may also be formed at a location where there is no insulating support 107. The trench 125 accurately defines the separation between the neighboring cMUT elements 102 and 104 (and thus the size of the transducer elements) to make the fabrication process easier.

The separation trench 125 may extend into the substrate 101 and connect to the top of the slot 105 in the substrate 101. The substrate 101 may be conductive and functions as a bottom electrode. Alternatively, a separate conductive layer (not shown) may be deposited on the substrate 101 to function as the bottom electrode. It is also appreciated that the insulation layer 108 is optional, and when used may also be deposited on the bottom surface of the membrane layer 110 facing the substrate 101.

The membrane layer 110 has a perimeter fixed or clamped on the insulating support 107. The rest of the membrane layer 110 is spaced from the substrate 101 to define a transducing gap 109. The transducing gap 109 is generally below the movable transducing member, which is the top electrode 120 in the embodiment shown, and above the substrate 101. Where there are intervening layers such as the membrane layer 110 and the insulation layer 108, it is appreciated that the transducing gap 109 is more precisely defined between the closest layers on two opposing sides of the gap. The membrane layer 110 vibrates in relation to the substrate 101 through the transducing 109 upon receiving a transducing excitation to perform transducing function.

As shown in FIG. 1A, the substrate 101 has a slot 105 opened through the bottom surface of the substrate 101. The slot 105 allows bending of the substrate. However, with the slot 105 alone, the entire cMUT structure 100 lacks support, making it difficult or impossible to handle the cMUT structure 100 during fabrication. The resultant cMUT structure 100 may also have inadequate integrity and mechanical soundness unless a special backing layer is provided. In addition, although the slot 105 physically allows bending of the substrate 101, it does not in itself provide any control of the actual bending process.

To solve the above problems, a soft or flexible material 106 is introduced into the slot 105 to at least partially fill the slot 105. The presence of the flexible material 106 in the slot 105 maintains the physical freedom for bending the substrate 101 yet at the same time provides needed support to the cMUT structure. In addition, as shown in other examples below, the flexible material 106 may further function as a bending actuator to provide a controllable force to bend the substrate 101.

The cMUT structure in the embodiment shown further has a flexible hinge 155 across the trench opening 125 between the surface portions (membrane layer 110 and the top electrode 120) of neighboring cMUT transducer elements 102 and 104. The flexible hinge 155 provides additional mechanical linkage between the neighboring cMUT transducer elements 102 and 104. In one embodiment, the flexible hinge 155 comprises a conductive material to provide necessary electrical connections between the neighboring transducer elements. Such electrical connections may be used for controlling or addressing the cMUT elements. The cMUT elements 102 and 104 may be individually addressable for certain applications but can also be collectively addressed as a single unit in other applications.

As will be shown in the description of fabrication methods, the filler material (not shown) may be used to at least partially fill the trench opening 125. The filler material may not hinder bending or angling of the neighboring cMUT transducer elements 102 and 104, but can provide additional support to the cMUT structure. In addition to providing mechanical support, the filler material in the trench opening 125 may also be designed to have a suitable acoustic property to reduce the acoustic coupling between the neighboring cMUT transducer elements 102 and 104 and to enhance other acoustic properties of the overall cMUT structure.

Examples of suitable materials for filling the slot 105 and the trench opening 125 may include, but not limited to, polyimide, polymer, PMMA, PDMS, SOG, epoxy, LTO, silicon nitride, Teflon, and Pryelene. In principle, the filler material may be any material which is compatible with the fabrication process, accommodates the bending requirement, and at least does not compromise the mechanical soundness and integrity of the cMUT structure. Preferably, the filler material is flexible and has a changeable size (e.g., shrinkable or expandable).

FIG. 1B shows a bent status of the cMUT structure 100. The substrate 101 is bent to form an angle between the two portions corresponding to the two neighboring cMUT elements 102 and 104. The surface portions (the membrane layer 110 and the top electrode 120) of the two neighboring cMUT elements 102 and 104 are also angled to each other. The flexible material 106 is compressed or shrunk to accommodate the bending.

To further accommodate bending, the slot 105 may have a nonuniform cross-sectional size that generally increases from the top surface to the bottom of the substrate 101. The slot 105 as shown in FIG. 1A has the shape of a wedge. However, no particular shape is required.

Correspondingly, when a shrinkable material 106 is used to fill the slot 105, the shrinkable material 106 may also have a nonuniform cross-sectional size along thickness of the substrate 101. With this configuration, the shrinkable material would be capable of undergoing a differential shrinkage in which the material in wider portions shrinks more than the material in narrower portions. Such differential shrinkage may effectuate bending of the substrate. The shrinkable material 106 filled in the slot 105 thus functions as a bending actuator to automatically bend the substrate 101 when triggered to shrink. The shrinkable material may start to shrink upon experiencing a change of environment, receiving a signal, or undergoing a treatment.

It is appreciated that instead of using a shrinkable material, an expandable material may be used for similar purpose. Given the same shape of the slot, using an expandable material causes the substrate to bend to an opposite direction. For this reason, a slot have different shape may be necessary to achieve similar bending, or a slot having a similar shape may be used to achieve bending at a different direction.

The bending actuator may be placed in the substrate of the transducer, as shown in the cMUT structure 100 in FIG. 1A. The bending actuator may also be built on a different portion of the substrate which is continuous to the substrate of the transducer elements. Furthermore, instead of building the bent actuator in the substrate itself, the bending actuator may be built in a separate layer in a similar way and placed underneath the substrate. As will be shown in other configurations below, in some embodiments the bending actuator is placed aside the substrate of the transducer elements.

The structure in FIG. 1A may be a flexible transducer array that has a general flexibility without requiring significant bending in a particular direction. In such embodiments, the slot 105 may not need to have a nonuniform cross-sectional size to accommodate large degree bending. For example, the slot 105 may be a trench with a substantially uniform cross-section size and still be able to afford a reasonable amount of flexibility of the substrate and the entire structure.

The above illustrated concept of the present invention may also be applied to cMUTs with embedded spring, or Embedded Spring Micromachined Ultrasonic Transducer (ESMUT) as described in the several PCT patent applications referenced herein. An exemplary transducer comprises: (1) a top plate; (2) a middle spring layer; and (3) a connector between the middle spring layer and the top plate. The top plate is placed over the connector, which separates the top plate from the middle spring layer; and the middle spring layer is placed over the substrate. The substrate and the middle spring layer define a cavity therebetween. The cavity is bordered by a standing feature having a sidewall; and the middle spring layer extends from the sidewall to cover the cavity.

Figure 2A:
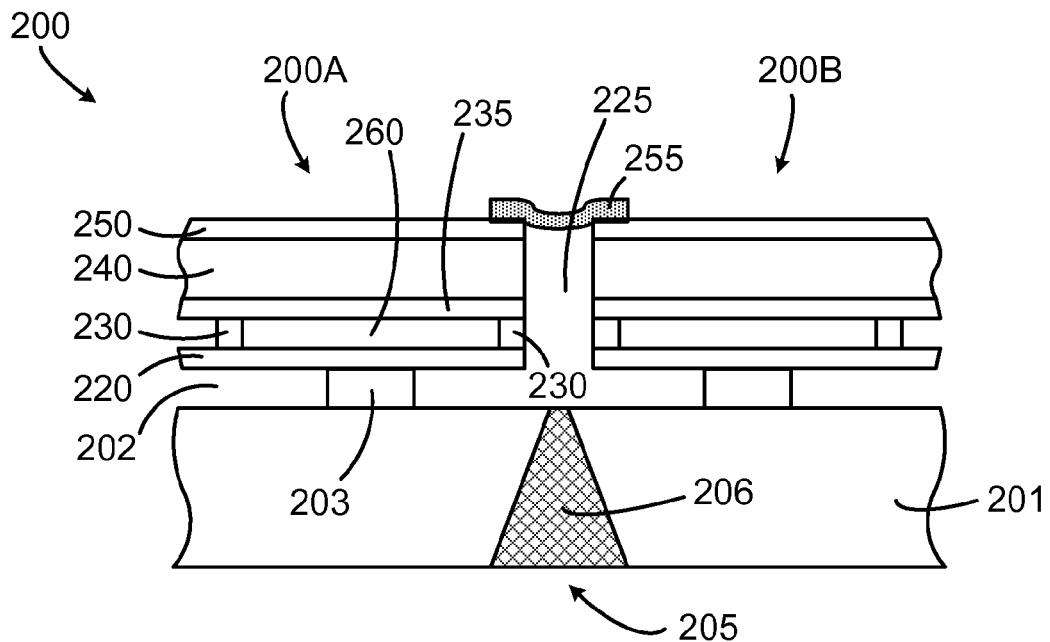
FIGS. 2A and 2B show an exemplary embodiment of the present invention improving the Embedded Spring Micromachined Ultrasonic Transducer (ESMUT).
Figure 2B:
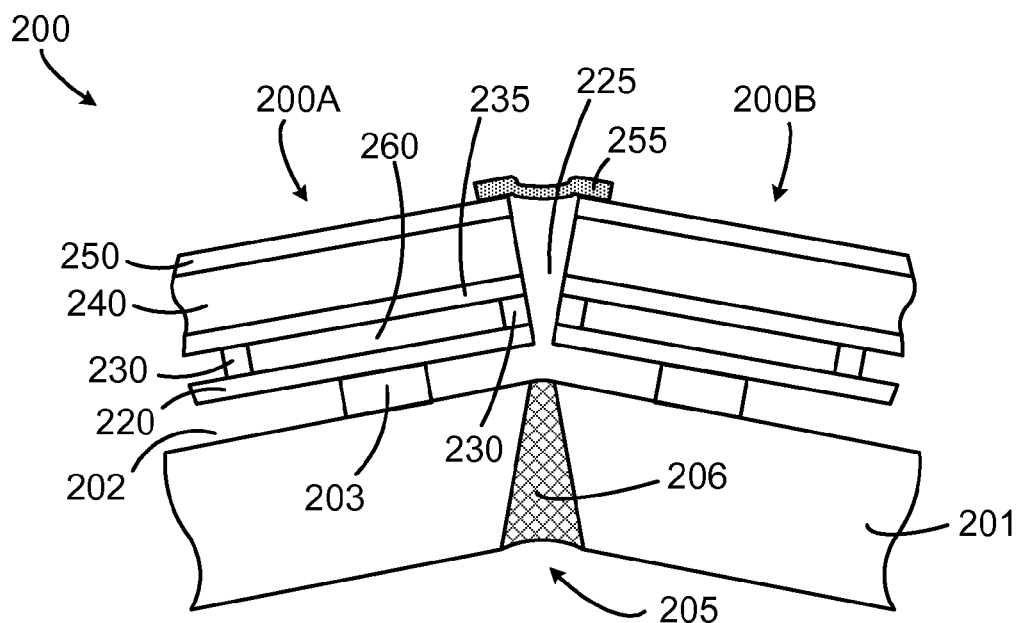

FIGS. 2A and 2B show an exemplary embodiment of the present invention improving the Embedded Spring Micromachined Ultrasonic Transducer (ESMUT). The ESMUT portion 200 is a part of a complete ESMUT element (not shown). Shown in FIGS. 2A and 2B are two ESMUT elements 200A and 200B which have similar structures. A description of the ESMUT element 200A generally applies to the ESMUT element 200B as well. The ESMUT portion 200 is built on a substrate 201, on top of which is a standing feature (referred to as "sidewall anchor" hereinafter) 203 having two sidewalls on two opposing sides bordering cavities 202. The standing feature (sidewall anchor) 203 may be an integrated part of the substrate 201 formed as a result of forming the cavities 202, but may also be an additional structure added onto a separate substrate. In one embodiment, for example, the sidewall anchor 203 is part of the middle spring layer 220. The substrate of 201 may be made of either a nonconductive material or a conductive material such as silicon or polysilicon. In a configuration where the sidewall anchor 203 is a separate structure, conductivity of the sidewall anchor 203 may be the same as or different from that of the substrate 201. For example, the substrate 201 may be made of a nonconductive material while the sidewall anchor 203 a conductive material such as metal, silicon or polysilicon.

Furthermore, the ESMUT elements 200A and 200B each have the following additional components: a middle spring layer 220 which is preferably an elastic membrane; connectors 230 which stand on top of the middle spring layer 220; an insulation layer 235 sitting over the connector 230; a top plate 240 connected to the connectors 230 through an intervening insulation layer 235; and a top electrode 250. In one embodiment, the middle spring layer 220 is conductive and serves as a bottom electrode. Alternatively, a separate bottom electrode (not shown) may be deposited on the middle spring layer 220. The bottom electrode may also be served by the substrate 201 itself if the substrate is conductive.

The bottom side of the top plate 240 faces the top side of the middle spring layer 220, and the bottom side of the middle spring layer 220 faces the front side of the substrate wafer, whereby the connector 230 stands out from the middle spring layer 220 to define a transducing space 260 below the top plate 240. The transducing space 260 is generally defined between the top plate layer 240 and the top surface of the middle spring layer 220 or the top surface of the sidewall anchor 203, whichever is higher. Where there is an intervening layer between the top plate layer 240 and the top surface of the middle spring layer 220 or the top surface of the sidewall anchor 203, the available transducing space may be reduced. For example, if another layer is deposited over the middle spring layer 220 or the sidewall anchor 203, the top surface of the sidewall anchor is defined as the uncovered surface of the layer deposited over the sidewall anchor 203.

Both substrate 201 including the sidewall anchor 203 and the middle spring layer 220 may be conductive. In this case, the substrate 201 may serve as a conductor to access the conductive middle spring layer 220, while the middle spring layer 220 may serve as the bottom electrode.

The connectors 230 stand on the middle spring layer 220 and each have substantially the same connector height. The connectors 230 are each horizontally distanced from the respective sidewall of the sidewall anchor 203 by a sufficient length. This defines two cantilevers each anchored at the respective side of sidewall anchor 203 with a back-to-back double cantilever formation. The cantilevers are activated through the respective connector 230 at an exerting end where the connector 230 is located. The cantilevers and the respective cavities 202 enable a vertical displacement of the connectors 230, which transport the top plate 240 substantially vertically with a piston-like motion, thus changing the transducing space 260. When the both cantilevers move in the same phase, the vertical piston-like motion is further assured.

Similar to the similar structure 100 shown in FIGS. 1A and 1B, a slot 205 is opened through the bottom surface of the substrate 201 to accommodate bending of the substrate. Furthermore, a soft or flexible material 206 is introduced into the slot 205 to at least partially fill the slot 205. The presence of the flexible material 206 in the slot 205 provides needed support and connection to the cMUT structure 200. In addition, the flexible material 206 may further function as a bending actuator to provide a controllable force to bend the substrate 101.

The cMUT structure further has a flexible hinge 255 across the trench opening 225 between the surface portions (including the top electrode 250, the top plate 240, the insulation layer 235, the connectors 230 and the middle spring layer 220) and the top electrode 120) of neighboring cMUT transducer elements 200A and 200B. The flexible hinge 255 provides additional mechanical linkage between the neighboring cMUT transducer elements 200A and 200B. In one embodiment, the flexible hinge 255 comprises a conductive material to provide necessary electrical connections between the neighboring transducer elements.

Similarly to FIG. 1B, FIG. 2B shows a bent status of the ESMUT structure 200.

Figure 3A:
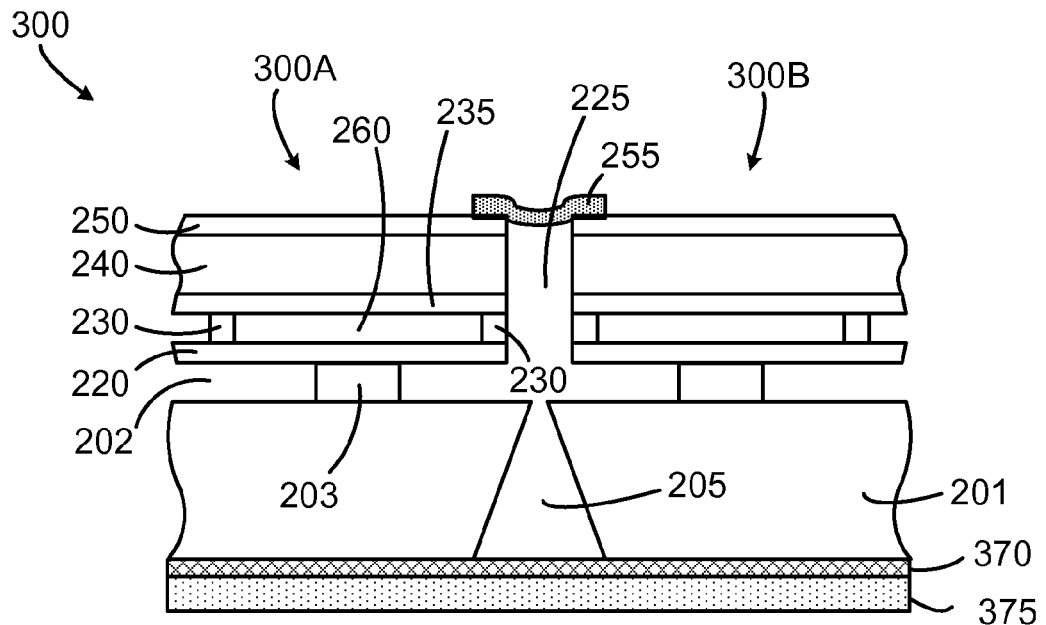
FIGS. 3A and 3B show a bending actuator using a bimorph structure.
Figure 3B:
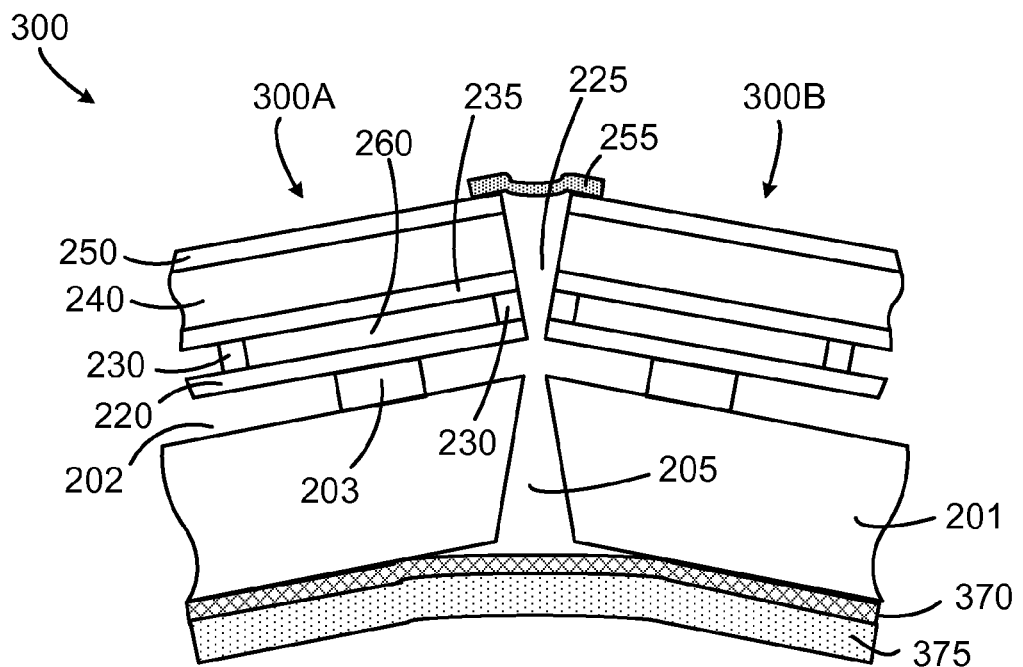

Other types of bending actuators may also be used. FIGS. 3A and 3B show an ESMUT 300 having an alternative bending actuator using a bimorph structure. The bending actuator is applied in an ESMUT for illustration, but it can also be applied to any other micro-electro-mechanical transducers including the conventional cMUT using a flexible membrane.

The ESMUT 300 is similar to the ESMUT 200 of FIGS. 2A and 2B, in which the similar components are denoted using the same or similar numbers. Unlike using the filler material to fill the slot 205, a bimorph structure having a first layer 370 and the second layer 375 is used as the bending actuator in ESMUT 300. When attached or bonded to the substrate 201, the bimorph structure (bimorph layers 370 and 375 as shown) is able to bend or curve the substrate 201.

Any bimorph structure that is capable of bending or deflect may be used. Various kinds of bimorph structures are known in the art and will not be described in detail here. Among the suitable bimorphs include piezoelectric bimorphs (or bimorph actuators) and thermal bimorphs. Piezoelectric bimorph actuators work based on the fact that two properly arranged (bonded and polarized) piezoelectric material deform in a way to cause a deflection when an electric field is applied in the right direction. Thermal bimorph actuators are based on two materials expanding or shrinking at different rates with temperature changes. The differential expansion or shrinkage causes a directional strain and thus makes the bimorph structure to bend or curve.

The bimorph structure can be formed (using coating or deposition techniques, for example) directly on the substrate. The bimorph structure can also be formed separately and bonded to the substrate.

FIGS. 4.1-4.9 show an exemplary process for fabricating a flexible cMUT in accordance with the present invention. The major steps of the process are described as follows.

In step one (FIG. 4.1), standing features 406 are formed on substrate 401. These standing features 406 will serve as support walls in the final cMUT structure. One way to form such standing features is to grow in patterned layer of an oxide.

In step two (FIG. 4.2), an insulation layer 408 is formed on substrate 401 over the pattern of standing features (support walls) 406. The standing features (support walls) 406 defying cavities 409 on the insulation layer 408 and the substrate 401.

In step three (FIG. 4.3), a trench 425 is formed from the front side through selected standing features 406 and the insulation layer 40 into the substrate 401. The selected standing futures 406 are located where the separation boundaries of neighboring cMUT elements are located. This may be preferable for more efficient use of the substrate area, but it is appreciated that cMUT elements may be separated at a location where there are no support walls.

In step four (FIG. 4.4), a membrane layer 410 is formed or placed over the side walls 406 to cover the cavities 409.

In step five (FIG. 4.5), a metal layer 420 is deposited over the membrane layer 410 and patterned if needed. This will be the top electrode, or be part of the top electrode, of the cMUT structure. In some embodiments, the membrane layer 410 is conductive and may not require a separate metal layer 420 as the top electrode.

In step six (FIG. 4.6), openings 426 are formed through the top electrode 420 and the membrane layer 410 to connect to the trench 425 previously formed. This allows the trench 425 to be filled with the filler material from the top. As will be shown in FIGS. 4.6*a* and 4.6*b*, in some embodiments openings 426 are patterned to leave the material of the top electrode 420 and the membrane layer 410 in selected areas unremoved to form a hinge structure connecting the two neighboring cMUT elements 400A and 400B over the opening 426 and the trench 425.

In step seven (FIG. 4.7), the trench 425 is filled or partially filled with a desired material 455. The filler material 455 should not completely hinder the flexibility between the two neighboring cMUT elements 400A and 400B. In addition, the filler material 455 may have proper acoustic properties to improve the acoustic decoupling between the neighboring cMUT elements. A preferable filler material 455 is soft or flexible. The filler material 455 may be parylene, PDMS, or any other suitable material. The filler material on the top surface of the electrode 420 (or the top surface of the membrane layer 410 if no separate top electrode is used) may be removed if needed.

In step eight (FIG. 4.8), a conductive layer 485 is deposited on the backside of the substrate 401.

In step nine (FIG. 4.9), a slot 405 with a desired pattern and shape is formed from the backside of the substrate 401. The slot 405 is then filled with a desired filler material 406. The filler material 406 should not hinder the flexibility between the two neighboring cMUT elements 400A and 400B. A preferable filler material 406 is soft or flexible. If needed, the wafer including the substrate 401 maybe thinned before etching slot 405 to facilitate etching process. The thinning may take place on the entire wafer or only areas where the slots 405 are to be formed.

FIGS. 4.6*a* and 4.6*b* show top views of two exemplary top surface opening formations in the cMUT structure in the above step six (FIG. 4.6). In FIG. 4.6*a*, openings 426 are patterned to leave the material of the top electrode 420 and the membrane layer 410 in selected areas unremoved to form a hinge 427 connecting the two neighboring cMUT elements CMUT1 (400A) and CMUT2 (400B) over the opening 426 and the trench 425. The top surface opening formation showing in FIG. 4.6*a* is only illustrative. Many other formations are may be used, as long as the opening the opening provides a channel to introduce a filler material into the trench 425 underneath and at the same time maintain its a certain level of flexibility to allow relative deflection or curving between the two neighboring cMUT elements. FIG. 4.6*b*, for example, shows an opening formation that is quite different from that in FIG. 4.6*a*. In FIG. 4.6*b*, small discrete holes 426 are formed through the top surface (the top electrode 420 and the membrane layer 410 in the particular embodiment shown in FIG. 4.6). Except for the holes 426, the four neighboring cMUT elements CMUT1, CMUT2, CMUT3 and CMUT4 are otherwise still connected through the original top surface material.

The basic concept of the present invention can be applied in a variety of micro-electro-mechanical transducer devices and applications. One example of such application is a 1-D array of cMUT elements, in which a plurality of the transducer elements are arranged side-by-side in succession to form an elongated strap which is closable or closed at two ends. In one embodiment, the elongated strap is closed at the two ends to form a substantially cylindrical shape, making possible a very compact cMUT probe having a range of applications including IVUS. A bending actuator also has an elongated shape arranged in parallel to the elongated strap of the transducer elements may be used. The bending actuator may have one or multiple elongated bending actuation member arranged in parallel to the elongated strap of the transducer elements on opposing sides thereof.

Figure 5:
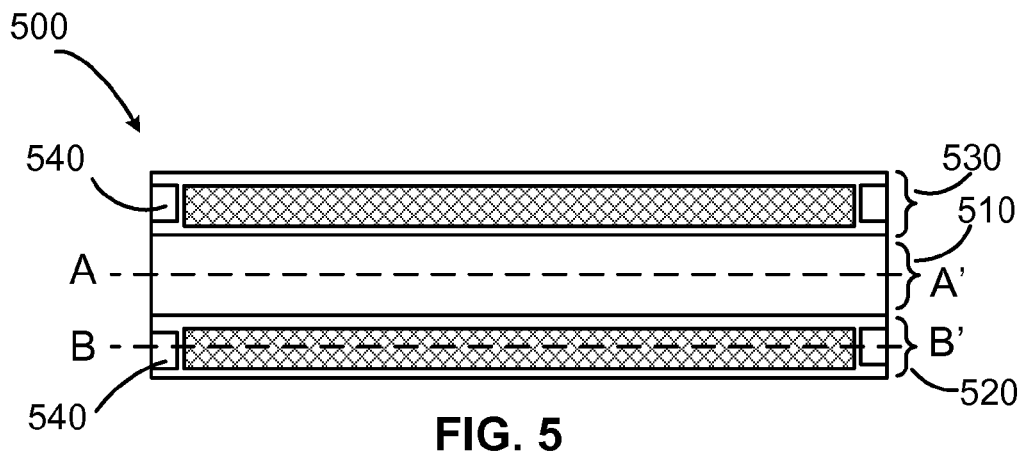
FIG. 5 shows a schematic top view of an exemplary flexible 1-D array of cMUT elements in accordance with the present invention.
Figure 6:
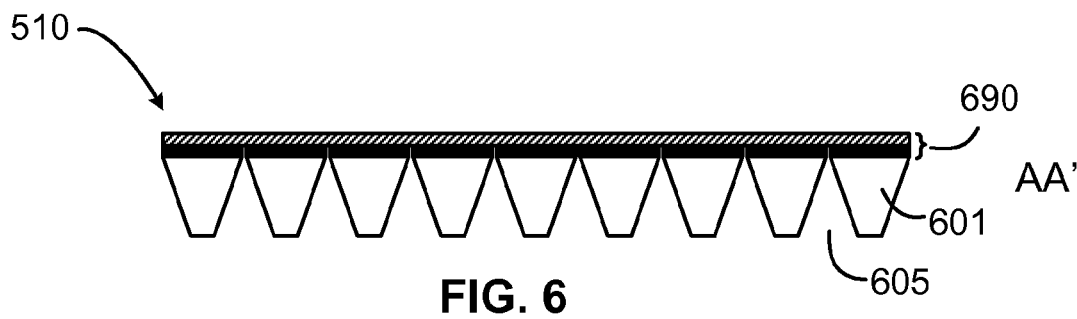
FIG. 6 shows a schematic cross-sectional view of a cMUT element band taken from dashed line A-A' in FIG. 5.

FIG. 5 shows a schematic top view of an exemplary flexible 1-D array of cMUT elements in accordance with the present invention. The 1-D cMUT array 500 has an overall elongated shape that comprises three bands (straps). In the middle is the cMUT element band 510 with an exemplary cross-sectional structure illustrated in FIG. 6. On the two opposing sides are two bending actuators 520 and 530 with a cross-sectional structure illustrated in FIGS. 7-8. The 1-D cMUT array 500 further has an optional latch structure 540 at both ends of the elongated strap to securely connect the two ends when the 1-D cMUT array 500 is bent to form a cylindrical shape as shown in FIGS. 6A-6C. An example of the latch structure 540 is illustrated in FIG. 9.

FIG. 6 shows a schematic cross-sectional view of the cMUT element band 510 taken from dashed line A-A' in FIG. 5. The cMUT element array 510 comprises multiple cMUT elements (not shown) built on the common substrate 601. Multiple slots 605 are formed on the substrate 601. Preferably, each slot 605 corresponds to one cMUT element, but any other distribution is permissible. The cMUT element array 510 has the surface portion collectively denoted as surface portion 690. The individual cMUT elements are built in the surface portion 690, and the actual structure of the surface portion 690 may be different with different cMUT designs. For example, if the ESMUT design as illustrated in FIGS. 2A and 2B is used, the surface portion 690 may be a multilayered structure as illustrated in FIGS. 2A and 2B.

Figure 7:
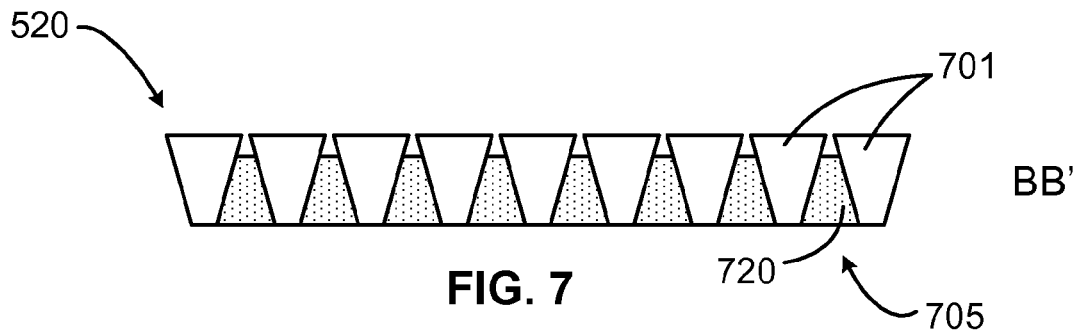
FIG. 7 shows a schematic cross-sectional view of an exemplary bending actuator.

FIG. 7 shows a schematic cross-sectional view of an exemplary bending actuator 520 or 530. The cross-sectional view of bending actuator 520 in FIG. 7 is taken from the dashed line B-B' in FIG. 5. The bending actuator 520 has a base layer 701 which has multiple actuation slots 705 filled with the bending actuation material 720. Preferably, actuation slots 705 have a one-to-one correspondence with the slots 605 on the substrate 601 of the cMUT element array 510 and are aligned with the respective slots 605 on the substrate 601. In the exemplary configuration shown, the base layer 701 of the bending actuator 520 is placed aside the substrate 601. The base layer 701 and the substrate 601 may originally belonged to two separate wafers and were brought together when the individually fabricated cMUT element array 510 and the bending actuators 520 and 530 are assembled or integrated as a single device. Alternatively, the base layer 701 and the substrate 601 may be portions of the same common substrate on which the cMUT element array 510 and the bending actuators 520 and 530 are fabricated either sequentially or simultaneously.

In the embodiment shown in FIG. 5, the bending actuator 520 is arranged aside the cMUT array 510. The base layer 701 and the substrate 601 may either be two separate layers or just different portions of the same contiguous substrate. The actuation slots 705 may preferably have a one-to-one correspondence with the slots 605 in the substrate. However, it is appreciated that such side-by-side arrangement is only illustrative and not required. For example, the bending actuator 520 may be directly built into the substrate 601 underneath the cMUT surface portion 690, instead of in a separate layer or portion 701. In this case, the bending actuation material 720 is filled into the slots 605 rather than into separate slots 705. Referring to FIGS. 6 and 7, in this particular embodiment the base layer 701 and the substrate 601 would be the same component, while the actuation slots 705 and the slots 605 would also be the same component.

Figure 8:
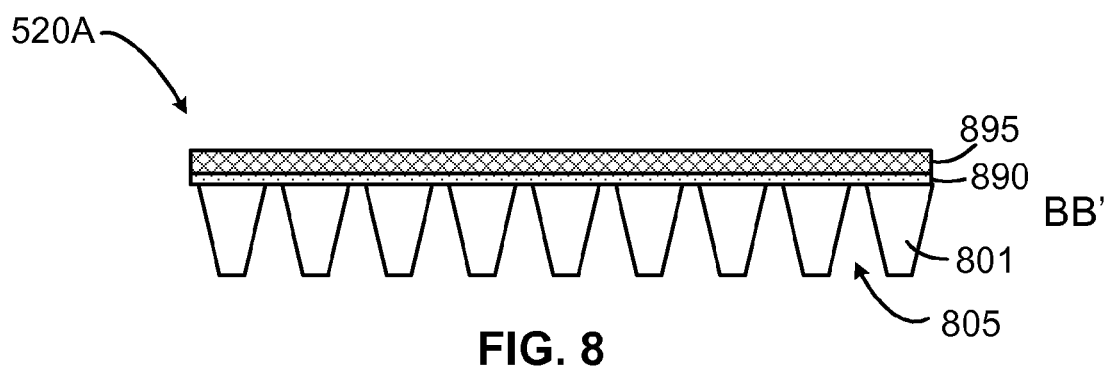
FIG. 8 shows a schematic cross-sectional view of another exemplary bending actuator.
Figure 9:
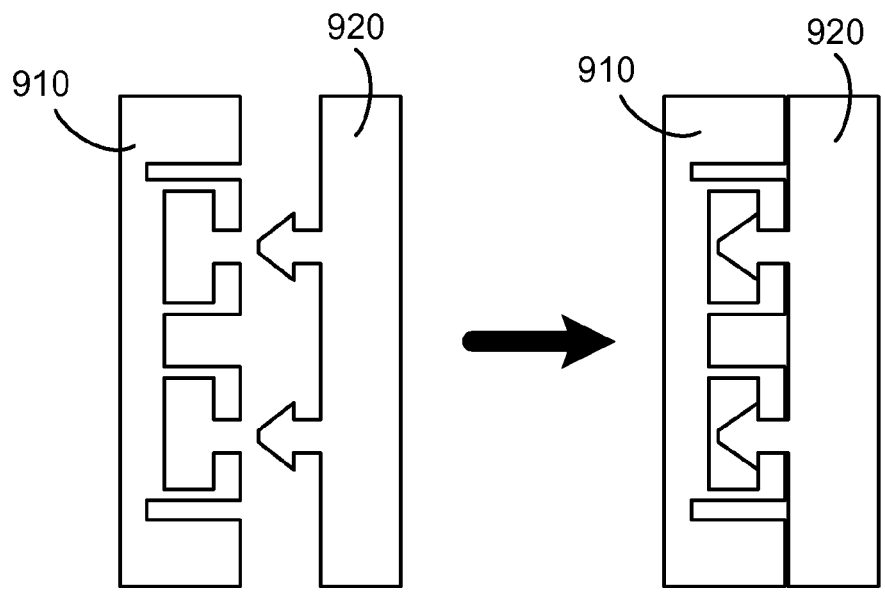
FIG. 9 shows an exemplary latch structure used at the ends of the elongated cMUT array shown in FIG. 5.

FIG. 8 shows a schematic cross-sectional view of another exemplary bending actuator 520 or 530. The cross-sectional view of bending actuator 520A in FIG. 8 is taken from the dashed line B-B' in FIG. 5. The bending actuator 520A may be a substitute of the bending actuator 520 illustrated above.

Similar to the bending actuator 520, the bending actuator 520A has a base layer 801 which has multiple actuation slots 805. Preferably, actuation slots 805 have a one-to-one correspondence with the slots 605 on the substrate 601 of the cMUT element array 510 and are aligned with the slots 605 on the substrate 601. Instead of using a filler material as the actuation material, the bending actuator 520A uses a bimorph actuator comprising two bimorph layers 890 and 895 to accomplish the bending of the substrate 601. The bimorph (890 and 895) may be placed on top of the base layer 801 as shown in FIG. 8, but may also be placed on bottom of the base layer 801. Regardless of the configuration, the bending direction exerted by the bending actuator should be chosen according to the design requirement for the bending of the substrate 801.

The two bending actuators 520 and 530 in FIG. 5 may both use one of the bending actuator designs shown in FIG. 7 and FIG. 8. Alternatively, the bending actuator 520 may use one design while the bending actuator 530 may use a different design.

The use of bending actuators 520 and 530 provides controllability to bend or curve the cMUT structure. In general, bending actuators may be designed to start to bend upon receiving a signal (such as an electrical signal for initiating a piezoelectric bimorph actuator), experiencing a change in environment (such as a change in temperature for initiating a thermal bimorph actuator or a thermally shrinkable/expendable material), or undergoing a treatment (such as a thermal treatment). The timing and the degree of bending can be controlled. The flexible cMUT in accordance with the present invention may be either curved during fabrication, or left uncurved until a later application time. The curved cMUT may be locked or fixed to make the curvature permanent, or remains flexible to allow adjustment of curvature during application.

FIGS. 6A, 7A and 8A show, respectively, a bent status of the cMUT element band 510, the exemplary bending actuator 520 and the exemplary bending actuator 520A. When bent inward, the 1-D cMUT element array forms a cylindrical shape with the cMUT elements formed on the surface portion of 690 radiating outward.

FIG. 9 shows an exemplary latch structure used at the ends of the elongated cMUT array 500 shown in FIG. 5. The two ends 910 and 920 have matching structures which when snapped together form a locking formation. Latching or locking at the ends is optional even if the cMUT array 500 is desired to be curved and fixed in a permanent position. For example, a backing layer (not shown) may be used to attach and support the cMUT strap 500, using a glue for example, to permanently fix the cMUT strap 500 in a curved formation.

As will be further illustrated below, particularly with reference to FIGS. 16.1-16.6 and FIGS. 17.1-17.2, the elongated cMUT array 500 may be further incorporated with an elongated array of IC components. The IC components may be fabricated on the same substrate of cMUT array (FIGS. 16.1-16.6). Alternatively, separately fabricated IC components and cMUT array may be subsequently assembled together (FIGS. 17.1-17.2).

Figure 10:
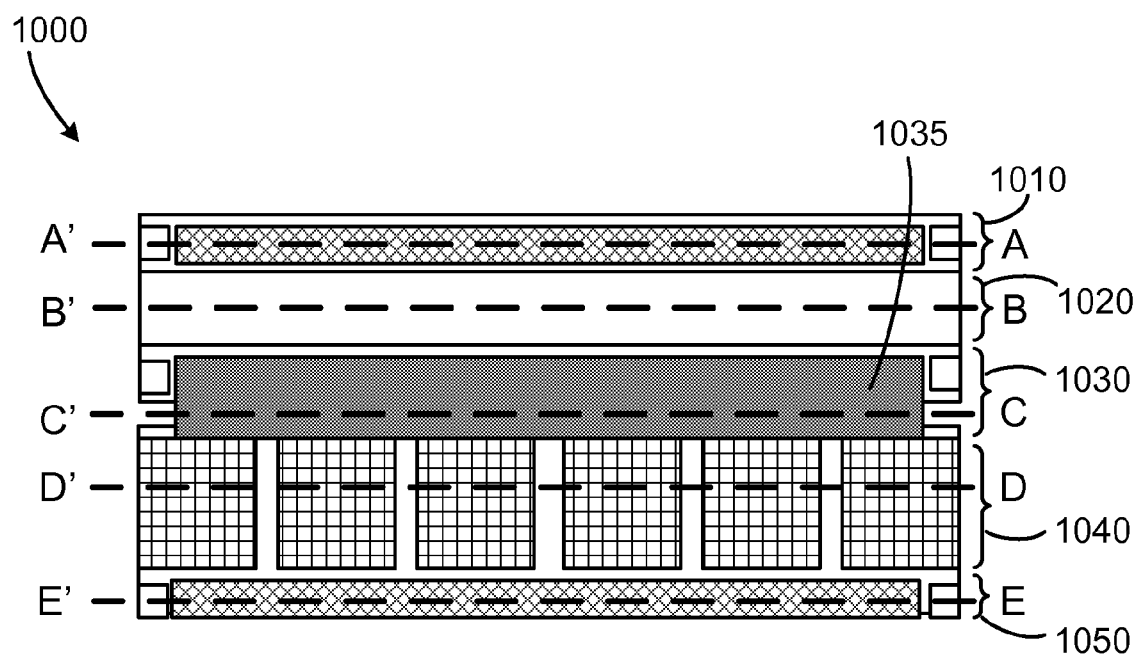
FIG. 10 shows an exemplary implementation of integration of a cMUT array with an IC component array in accordance with the present invention.

FIG. 10 shows an exemplary implementation of integration of a cMUT array with an IC component array in accordance with the present invention. The integrated cMUT array 1000 generally has five bands. From top to bottom are bending actuator 1010, cMUT element band 1020, IC interface band 1030 which comprises a flexible cable 1035, IC component band 1040, and another bending actuator 1050.

Figure 11:
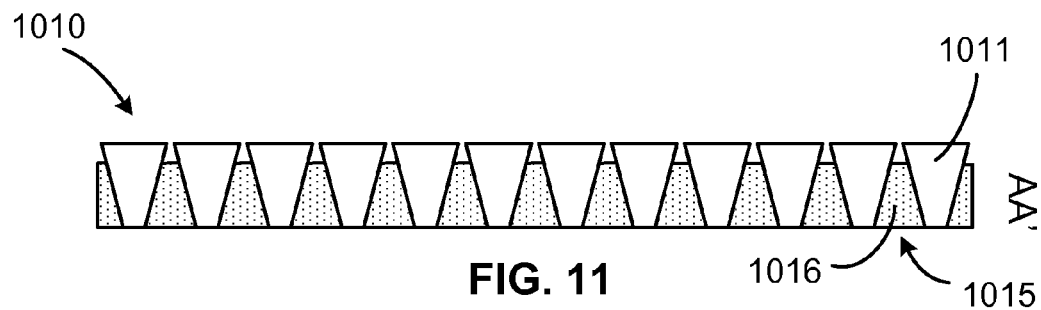
FIG. 11 shows a cross-sectional view of an exemplary configuration of a first bending actuator to control the bending of the CMUT array in the integrated cMUT array shown in FIG. 10.

FIG. 11 shows a cross-sectional view of an exemplary configuration of the bending actuator 1010 in the integrated cMUT array 1000. The cross-sectional view is taken from the dashed line AA' in FIG. 10. The bending actuator 1010 is built on a base layer 1011 which has a plurality of slots 1015 filled with a soft or flexible material 1016. Other suitable bending actuation mechanisms may also be used. In addition to using a thermally shrinkable/expendable, other types of actuation such as piezoelectric bimorph and thermal bimorph may also be used.

Figure 12:
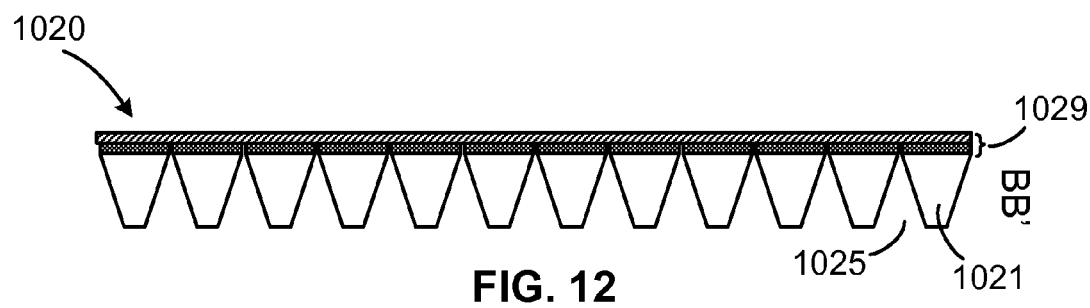
FIG. 12 shows a cross-sectional view of an exemplary configuration of the cMUT element band shown in FIG. 10.

FIG. 12 shows a cross-sectional view of an exemplary configuration of the cMUT element band 1020. The cross-sectional view is taken from the dashed line BB' in FIG. 10. The cMUT element band 1020 can use a configuration similar to that of the cMUT element band 510 shown in FIG. 6. The cMUT element array 1020 comprises multiple cMUT elements (not shown) built on the common substrate 1021. Multiple slots 1025 are formed on the substrate 1021. Preferably, each slot 1025 corresponds to one cMUT element, but any other distribution is permissible. The cMUT element band 1020 has a surface portion collectively denoted as surface portion 1029. The individual cMUT elements are built in the surface portion 1029, and the actual structure of the surface portion 1029 may be different with different cMUT designs. For example, if the ESMUT design as illustrated in FIGS. 2A and 2B is used, the surface portion 1029 may be a multilayered structure as illustrated in FIGS. 2A and 2B.

Figure 13:
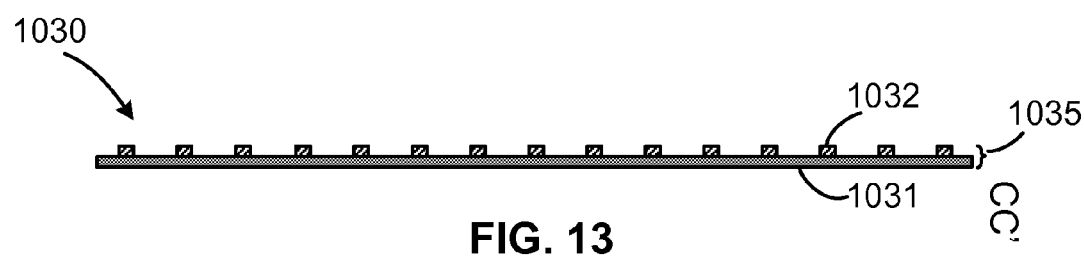
FIG. 13 shows a cross-sectional view of an exemplary configuration of a flexible cable, which forms an interface between the cMUT element array and the IC component band shown in FIG. 10.

FIG. 13 shows a cross-sectional view of an exemplary configuration of the IC interface band 1030, which forms an interface between the cMUT element array 1020 and the IC component band 1040 to both mechanically and electrically connect the two bands. The cross-sectional view is taken from the dashed line CC' in FIG. 10. The IC interface band 1030 has a thin base layer 1031 and narrow connecting cables 1032, which are collectively denoted as IC connection cable 1035. The IC connection cable 1035 is preferably flexible. Such flexibility is particularly useful when the bending characteristics of the cMUT element band 1020 and the IC component band 1040 are different. For example, the number of slots 1025 in the substrate of the cMUT element band 1020 may be different from the number of slots 1045 in the substrate of the IC component band 1040, and as a result the two bands 1020 and 1040 may not be bent exactly uniformly, thus requiring a certain degree of flexibility of the interface band 1030 therebetween.

The function and the structure of the IC interface band 1030 are better understood in the description of the fabrication process with references to FIGS. 16.1-16.6. The IC interface band 1030 may be an add-on component to connect separately formed cMUT element band 1020 and IC component band 1040. However, preferably the cMUT element band 1020 and the IC component band 1040 are fabricated on a common substrate and integrated process instead of separately, and the corresponding IC interface band 1030 may be formed as an integral part of the fabrication process of cMUT element band 1020 the IC component band 1040. This will be further illustrated below with references to FIGS. 16.1-16.6.

Figure 14:
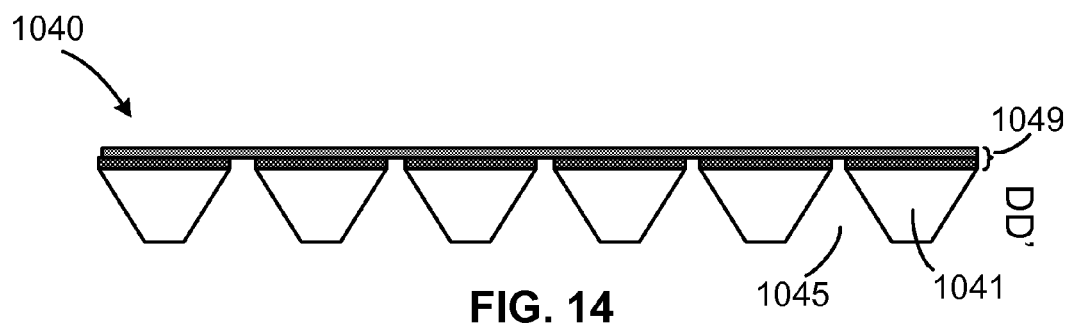
FIG. 14 shows a cross-sectional view of an exemplary configuration of the IC component band shown in FIG. 10.

FIG. 14 shows a cross-sectional view of an exemplary configuration of the IC component band 1040. The cross-sectional view is taken from the dashed line DD' in FIG. 10. The IC component band 1020 comprises multiple IC components (not shown) built in IC layers collectively denoted as 1049. The multiple IC components share a common substrate 1041. Multiple slots 1045 are formed on the substrate 1041 to accommodate bending of the substrate 1041 in a way similar to what the slots 1025 do to the cMUT element band 1020 in FIG. 12. Preferably, each slot 1025 corresponds to one IC component, but any other distribution is permissible. Because the number of IC components may be different from the number of cMUT elements (for example, a single IC component may correspond to, and control, multiple cMUT elements), the number of slots 1045 may be different from the number of slots 1025.

Figure 15:
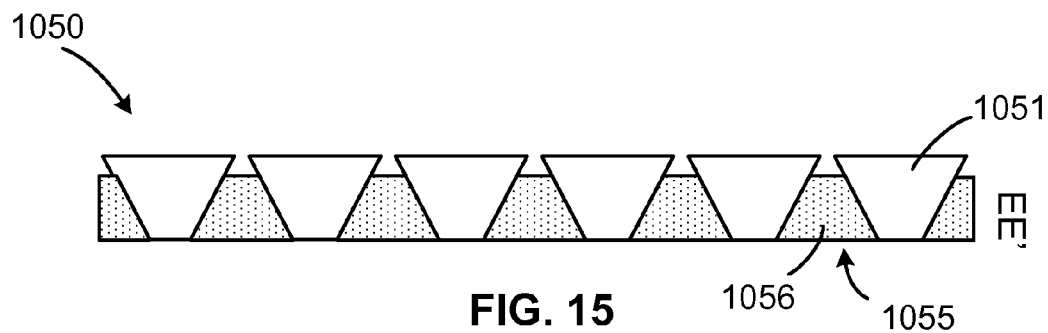
FIG. 15 shows a cross-sectional view of an exemplary configuration of a second bending actuator to control the bending of IC component band in the integrated cMUT array shown in FIG. 10.
Figure 11A:
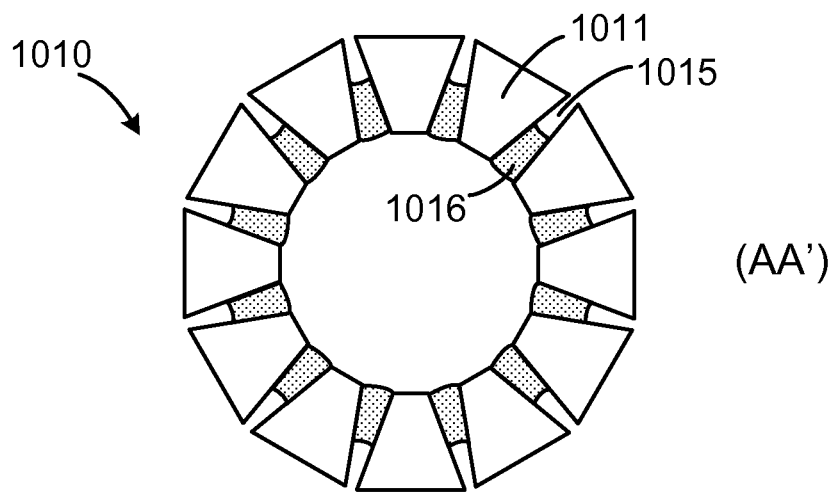
FIG. 11A shows an exemplary bent status of the first bending actuator in the integrated cMUT array shown in FIG. 10.
Figure 12A:
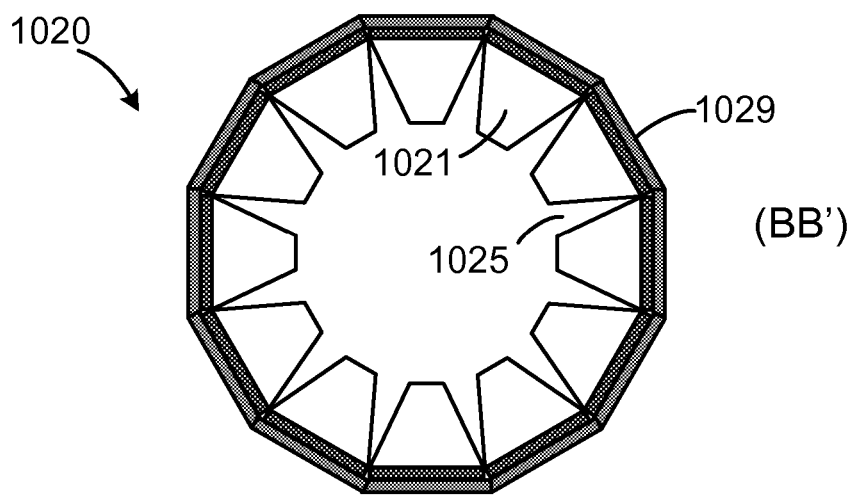
FIG. 12A shows an exemplary bent status of the cMUT element band in the integrated cMUT array shown in FIG. 10.
Figure 14A:
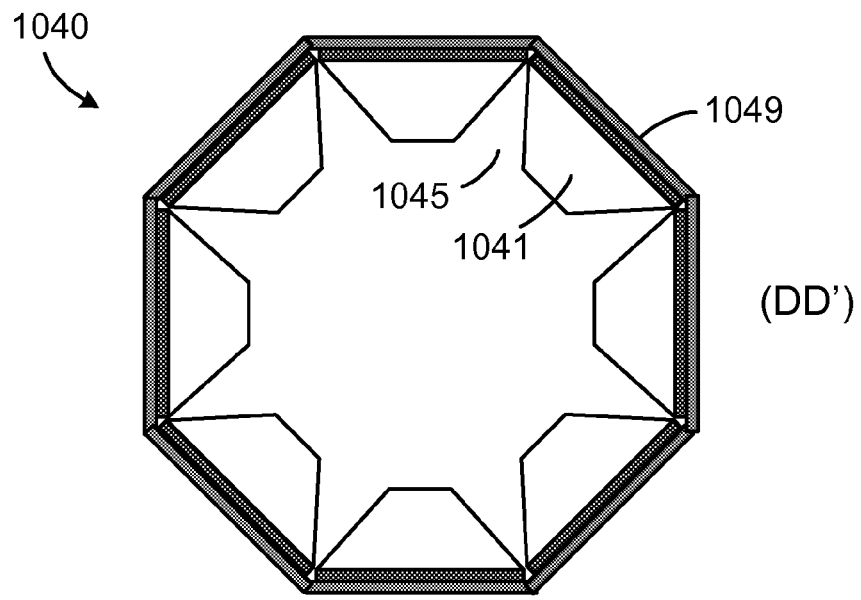
FIG. 14A shows an exemplary bent status of the IC component band in the integrated cMUT array shown in FIG. 10.
Figure 15A:
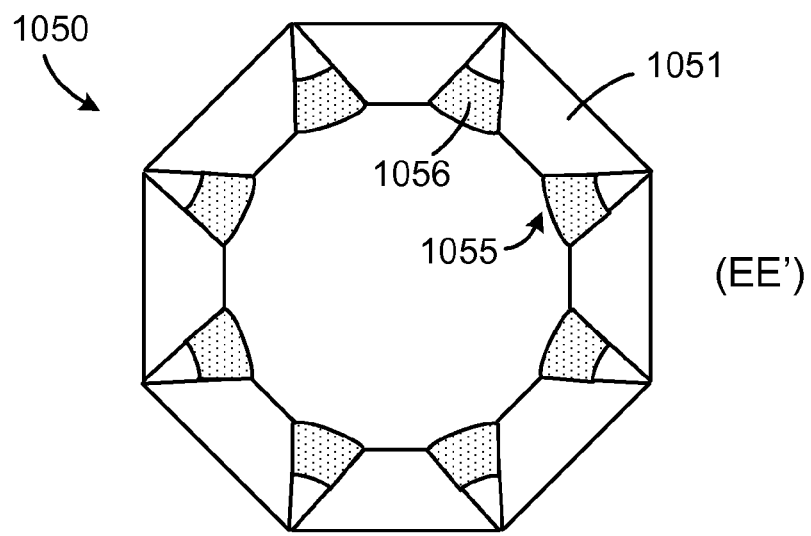
FIG. 15A shows an exemplary bent status of the second bending actuator in the integrated cMUT array shown in FIG. 10.

FIG. 15 shows a cross-sectional view of an exemplary configuration of the bending actuator 1050 in the integrated cMUT array 1000. The cross-sectional view is taken from the dashed line EE' in FIG. 10. The bending actuator 1050 is built on a base layer 1051 which has a plurality of slots 1055 filled with a soft or flexible material 1056. In a preferred embodiment, the number of the slots 1055 is the same as the number of slots 1045 in the IC component band 1040, and each slot 1055 is aligned with a respective slot 1045. The number of the slots 1055 in the bending actuator 1050 and the number of slots 1015 in the bending actuator 101 may not be the same. Any other suitable bending actuation mechanism may also be used. In addition to using a thermally shrinkable/expendable, other types of actuation such as piezoelectric bimorph and thermal bimorph may also be used. Furthermore, the bending actuator 1050 and the bending actuator 1010 may either use the same or different bending mechanisms.

FIGS. 11A, 12A, 14A and 15A show, respectively, a bent status of the bending actuator 1010, the cMUT element band 1020, the IC component band 1040 and the bending actuator 1050, respectively. When bent inward, the 1-D cMUT element array forms a cylindrical shape with the cMUT elements formed on the surface portion of 1029 radiating outward.

The cMUT array and IC components may be integrated in the same substrate if the fabrication processes of both cMUT and IC components are compatible. Alternatively, separately fabricated IC may be assembled into a substrate with a cMUT array. FIGS. 16.1-16.6 show an exemplary process for assembling an IC die with prefabricated IC components into a substrate with a cMUT array. The major steps of the process are described as follows.

In step one (FIG. 16.1), cMUTs 1610 are formed on a wafer based on substrate 1601.

In step two (FIG. 16.2), a trench 1620 is formed through the surface portion and partially through the substrate 1601 to place IC dies. Optionally, a clamping structure 1625 may be fabricated at the same time.

In step three (FIG. 16.3), an IC die 1630 is placed into the trench 1620 and is positioned by the clamping structure 1625.

In step four (FIG. 16.4), a filler material 1640 is coated and patterned over the voids left by IC die 1630 and over the top surface of the wafer to form a surface layer 1645. The filler material 1640 may be a similar material to the material used to fill the trenches in the cMUT surface portions (e.g., the filler material 455 in FIG. 4.7). Examples of suitable materials include, but not limited to, pryelene, polyimide, polymer, LTO, silicon nitride, Teflon, SOG, photoresist, and epoxy. The coated and patterned surface layer 1645 of the filler material 1640 will become the thin base layer (such as 1031 in FIG. 13) in the IC interface band in a later step (the step six in FIG. 16.6).

In step five (FIG. 16.5), a metal layer 1650 is deposited and patterned over the surface layer 1645 and also over the surface of the cMUTs 1610. The metal layer 1650 in the areas of the cMUTs 1610 may be used as the top electrodes or part thereof. The metal layer 1650 in the areas between the cMUTs 1610 and the IC die 1630 becomes the thin connection layer (such as 1032 in FIG. 13) in the IC interface band in a later step (the step six in FIG. 16.6) to connect the cMUTs and the IC's.

In step six (FIG. 16.6), a trench 1660 is etched to form a flexible MEMS bridge connection (a flexible cable) including the thin base layer 1645 and thin metal layer 1650 to connect cMUTs and IC dies.

If there is compatibility between the process for fabricating cMUTs and the process for fabricating ICs, the cMUTs and the ICs may be directly fabricated on the same substrate. An example of this direct fabrication method is illustrated in FIGS. 17.1-17.2. As shown in FIG. 17.1, IC components 1730 are directly fabricated on the substrate 1701 on which the cMUT elements 1710 are also formed. As shown in FIG. 17.2, surface layer 1745 similar to the surface layer 1645 in FIG. 16.6 is formed. Metal layer 1750 similar to the metal layer 1650 in FIG. 16.6 is also formed. Likewise, a trench 1760 is etched to form a flexible MEMS bridge connection (a flexible cable) including thin surface layer 1745 and thin metal layer 1750 to connect cMUTs 1710 and ICs 1730.

The above fabrication processes can be used to integrate IC components with any suitable micro-electro-mechanical transducers, including cMUTs of membrane-based designs and embedded spring based ESMUTs.

The micro-electro-mechanical transducer in accordance with the present invention has been described in detail along with the figures and exemplary embodiments. The transducer potentially can alleviate or eliminate a number of problems with existing technology. The invention has eliminated the necessity of forming an addressable transducer element using a great number of smaller cells. Using the technology, either a much fewer cells are just a single cell may be necessary for each addressable transducer element. The design of the micro-electro-mechanical transducer of the present invention is particularly suitable for application in capacitance micro-machined ultrasonic transducers (cMUT), but can also be used for other micro-electromechanical devices which have a movable mechanical part to transform energy.

In particular, the micro-electro-mechanical transducer in accordance with the present invention may be fabricated using the fabrication methods or incorporated in the micro-electro-mechanical transducer is disclosed in international patent applications (PCT) No. PCT/IB2006/051566, entitled THROUGH-WAFER INTERCONNECTION, filed on May 18, 2006; No. PCT/IB2006/051567, entitled METHODS FOR FABRICATING MICRO-ELECTRO-MECHANICAL DEVICES, filed on May 18, 2006; No. PCT/IB2006/051568, entitled MICRO-ELECTRO-MECHANICAL TRANSDUCERS, filed on May 18, 2006; No. PCT/IB2006/051569, entitled MICRO-ELECTRO-MECHANICAL TRANSDUCERS, filed on May 18, 2006; and No. PCT/IB2006/051948, entitled MICRO-ELECTRO-MECHANICAL TRANSDUCER HAVING AN INSULATION EXTENSION, filed on Jun. 16, 2006. These patent applications are hereby incorporated herein by reference.

In the foregoing specification, the present disclosure is described with reference to specific embodiments thereof, but those skilled in the art will recognize that the present disclosure is not limited thereto. Various features and aspects of the above-described disclosure may be used individually or jointly. Further, the present disclosure can be utilized in any number of environments and applications beyond those described herein without departing from the broader spirit and scope of the specification. We claim all such modifications and variations that fall within the scope and spirit of the claims below. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A micro-electro-mechanical transducer comprising:
a substrate of a substrate material;
a plurality of transducer elements built on the substrate, each transducer element having a surface portion including a movable transducing member, the surface portion being spaced from the substrate to define a transducing gap between the movable transducing member and the substrate;
a slot passing entirely through the substrate to separate the substrate into neighboring portions that are not connected to each other by the substrate material, wherein the neighboring portions of the substrate form opposing walls of the slot; and
a flexible material within the slot, the flexible material contacting the opposing walls of the slot to provide a structural connection between the neighboring portions of the substrate separated by the slot, the flexible material able to maintain structural integrity of the structural connection between the neighboring portions of the substrate during bending of the transducer to allow positioning of the neighboring portions of the substrate at an angle relative to each other.

2. The micro-electro-mechanical transducer of claim 1 wherein the plurality of the transducer elements are arranged side-by-side in succession to form an elongated strap that is flexible, closable or closed at two ends.

3. The micro-electro-mechanical transducer of claim 1, wherein the slot has a non-uniform cross section to allow positioning of the neighboring portions of the substrate at the angle relative to each other.

4. The micro-electro-mechanical transducer of claim 3, wherein the slot increases in cross section toward a side of the substrate opposite to the transducer elements.

5. The micro-electro-mechanical transducer of claim 4 further comprising a trench separating neighboring transducer elements, wherein the trench is at least partially filled with a filler material that extends at least partially over the surface portion of the neighboring transducing elements.

6. The micro-electro-mechanical transducer of claim 4 further comprising a trench separating neighboring transducer elements, wherein the trench is located between two neighboring transducer elements to define a bending position.

7. The micro-electro-mechanical transducer of claim 4, further comprising a trench separating neighboring transducer elements, wherein the trench extends to the slot formed through the substrate to separate the transducer elements and corresponding portions of the substrate from neighboring transducer elements and corresponding portions of the substrate.

8. The micro-electro-mechanical transducer of claim 1, wherein:
the substrate material is conductive and forms, at least in part, respective electrodes of respective transducer elements, and
the flexible material is at least one of dielectric or insulative.

9. The micro-electro-mechanical transducer of claim 1, wherein the flexible material in the slot is at least one of shrinkable or expandable to automatically cause the bending of the transducer.

10. The micro-electro-mechanical transducer of claim 1, wherein the flexible material in the slot is triggered to generate a force to cause the bending of the transducer in response to, at least in part, at least one of a change in temperature, or receiving an electromagnetic signal.

11. The micro-electro-mechanical transducer of claim 1 further comprising:
a trench separating neighboring transducer elements; and
a flexible hinge across the trench, the flexible hinge comprising a conductive material to electrically connect the neighboring transducer elements.

12. The micro-electro-mechanical transducer of claim 1 wherein the flexible material in the slot has a nonuniform cross-sectional size along a thickness of the substrate such that the flexible material is capable of undergoing an automatic differential change in size, the change in size of the flexible material causing, at least in part, the bending of the transducer to position the adjacent portions of the substrate at the angle relative to each other.

13. The micro-electro-mechanical transducer of claim 1, wherein:
individual transducer elements are capacitive micromachined ultrasound transducer (cMUT) elements,
the transducing member comprises a top electrode, and
the individual transducer elements further comprise a respective bottom electrode spaced from the top electrode.

14. The micro-electro-mechanical transducer of claim 1 wherein the surface portion of an individual one of the transducer elements comprises:
a top plate;
a middle spring layer; and
a connector between the middle spring layer and the top plate, wherein the top plate is placed over the connector, which separates the top plate from the middle spring layer, and wherein the middle spring layer is placed over the substrate, the substrate and the middle spring layer defining a cavity therebetween, the cavity being bordered by a standing feature having a sidewall, the middle spring layer extending from the sidewall to cover the cavity.

15. A micro-electro-mechanical transducer comprising:
a substrate;
a plurality of transducer elements built on the substrate, each transducer element having a surface portion including a movable transducing member, the surface portion being spaced from the substrate to define a transducing gap between the movable transducing member and the substrate;
a slot formed through the substrate between each transducer element;
a flexible material in the slot, the flexible material connecting a first portion of the substrate to a second portion of the substrate to enable the first portion of the substrate to bend relative to the second portion of the substrate; and
a bending actuation material actuable to at least one of shrink or expand to generate a force to position the first portion of the substrate at an angle relative to the second portion of the substrate.

16. The micro-electro-mechanical transducer of claim 15 wherein the bending actuation material automatically positions the first portion of the substrate relative to the second portion the substrate in response, at least in part, to receiving an electromagnetic signal.

17. The micro-electro-mechanical transducer of claim 16 wherein the bending actuation material automatically positions the first portion of the substrate relative to the second portion the substrate in response, at least in part, to a change of temperature.

18. The micro-electro-mechanical transducer of claim 15 wherein the flexible material filled in the slot includes, at least in part, the bending actuation material.

19. The micro-electro-mechanical transducer of claim 15 wherein the bending actuation material is disposed on an actuator substrate that is contiguous to the substrate of the transducer elements.

20. The micro-electro-mechanical transducer of claim 19 wherein:
the actuator substrate has an actuation slot aligned with the slot on the substrate of the transducer elements; and
the bending actuation material is disposed, at least in part, in the actuation slot.

21. The micro-electro-mechanical transducer of claim 15 wherein:
the plurality of the transducer elements are arranged side-by-side in succession to form an elongated strap which is closable or closed at two ends; and
the bending actuation material has an elongated shape arranged in parallel to the elongated strap of the transducer elements.

22. The micro-electro-mechanical transducer of claim 15 wherein the bending actuation material comprises a bimorph material.

23. A curved micro-electro-mechanical transducer comprising:
a substrate;
a plurality of transducer elements built on the substrate, each transducer element having a surface portion including a movable transducing member, the surface portion being spaced from the substrate to define a transducing gap between the movable transducing member and the substrate;
a slot opened through the substrate to separate the substrate into neighboring portions that are not connected by substrate material; and
a flexible material in the slot, the flexible material connecting opposing walls of the slot to provide a structural connection between the neighboring portions of the substrate that are separated by the slot, wherein the flexible material is able to maintain the structural connection between the neighboring portions of the substrate, while permitting the neighboring portions of the substrate to be positioned at an angle relative to each other.

24. The curved micro-electro-mechanical transducer of claim 23 wherein the plurality of the transducer elements are arranged side-by-side in succession to form a curved strap that is closed or near closed at two ends.

25. The curved micro-electro-mechanical transducer of claim 23 wherein the slot has a non-uniform cross section to allow positioning of the neighboring portions of the substrate at the angle relative to each other.

26. The curved micro-electro-mechanical transducer of claim 23 further comprising a bending actuation material actuable to automatically position the neighboring portions of the substrate relative to each other.

27. The curved micro-electro-mechanical transducer of claim 26 wherein the bending actuation material is actuable to automatically cause positioning of the neighboring portions of the substrate in response to, at least in part, at least one of a change in temperature, or receiving an electromagnetic signal.

28. A bent or bendable capacitive micromachined ultrasound transducer (cMUT) array comprising:
a substrate;
a plurality of cMUT elements built on the substrate, the cMUT elements being arranged side-by-side in succession to form an elongated cMUT array, each cMUT element having a surface portion spaced from the substrate, each cMUT element including a top electrode and a bottom electrode, the bottom electrode spaced from the top electrode to define a transducing gap therebetween; and
a plurality of slots formed entirely through the substrate to separate the substrate into neighboring substrate portions and to provide a slot of the plurality of slots located below a border between two neighboring transducer elements to accommodate bending of the elongated cMUT array; and
a flexible material in each slot to structurally connect the neighboring substrate portions separated by the slots, such that, when the elongated cMUT array is bent, the neighboring substrate portions are angled with respect to each other, wherein structural integrity of the elongated cMUT array is maintained by the flexible material structurally connecting the neighboring substrate portions so that the elongated cMUT array is capable of forming an overall cylindrical shape.

29. The bent or bendable cMUT array of claim 28 further comprising an elongated bending member parallel to the elongated cMUT array, the bending member being adapted for automatically bending or adjusting bending of the elongated cMUT array upon experiencing at least one of: a change of environment, receiving a signal or undergoing a treatment.

30. The bent or bendable cMUT array of claim 28 adapted for use as an intravascular ultrasound (IVUS) device.

31. The bent or bendable cMUT array of claim 28 further comprising an elongated array of IC components built on an IC substrate arranged in parallel with the elongated cMUT array of cMUT elements.

32. The bent or bendable cMUT array of claim 31 wherein the elongated array of IC components is placed side-by-side to the elongated cMUT array of cMUT elements and connected thereto with a thin and flexible layer.

33. The bent or bendable cMUT array of claim 31 wherein the IC substrate and the substrate for the cMUT elements are a common substrate.

34. The bent or bendable cMUT array of claim 31 wherein the IC substrate comprises an IC die placed into a hosting cavity formed in the substrate of the bent or bendable cMUT array.

35. A method for making a flexible or bent micro-electro-mechanical transducer, the method comprising:
fabricating a plurality of capacitive micromachined ultrasound transducer (cMUT) elements on a top surface of a substrate, each cMUT element having a surface portion including a movable transducing member, the surface portion being spaced from the substrate to define a transducing gap between the movable transducing member and the substrate;
forming a slot entirely through the substrate to separate the substrate into multiple neighboring portions; and
disposing a flexible material in at least a portion of the slot to structurally connect the multiple neighboring portions of the substrate to each other, wherein the flexible material maintains, at least in part, structural connection between the neighboring portions of the substrate of the micro-electro-mechanical transducer while permitting bending of the micro-electro-mechanical transducer to angle the multiple neighboring portions of the substrate relative to each other.

36. The method of claim 35 wherein the flexible material is shrinkable or expandable in response to at least one of a change in temperature or an electromagnetic signal, the method further comprising: shrinking or expanding the flexible material to bend the micro-electro-mechanical transducer to angle the multiple portions of the substrate relative to each other.

37. The method of claim 35 further comprising:
introducing a bending actuation material along the substrate; and
automatically bending or changing bending of the micro-electro-mechanical transducer by actuating the bending material with at least one of: a change of environment, receiving a signal, or undergoing a treatment.

38. The method of claim 35 further comprising:
forming a trench through the surface portion to separate neighboring transducer elements; and
disposing a filler material in at least a portion of the trench.

39. The method of claim 35 further comprising:
prior to forming the surface portion, forming a trench in the top surface of the substrate;
disposing a membrane layer and an electrode layer over the substrate to form the surface portion; and
forming the slot from a bottom side of the substrate, wherein the slot through the substrate connects to the trench.

* * * * *